(12) United States Patent
Woodward et al.

(10) Patent No.: US 6,395,787 B1
(45) Date of Patent: May 28, 2002

(54) OCULAR HYPOTENSIVE LIPIDS

(75) Inventors: David F. Woodward, Lake Forest; Helen H. Usansky, Irvine; Steven W. Andrews, Rancho Santa Margarita; Robert M. Burk, Laguna Beach; June Chen, San Juan Capistrano; Achim H-P. Krauss, Foothill Ranch, all of CA (US); Cherukury Madhu, Des Plaines, IL (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/500,142

(22) Filed: Feb. 8, 2000

(51) Int. Cl.[7] .................... A61K 31/5575; C07C 405/00
(52) U.S. Cl. ....................... 514/613; 514/622; 564/171; 564/189
(58) Field of Search ................................ 564/189, 171; 514/613, 622

(56) References Cited

U.S. PATENT DOCUMENTS

| | | | |
|---|---|---|---|
| 5,288,754 A | 2/1994 | Woodward et al. | 514/530 |
| 5,353,708 A | 10/1994 | Woodward et al. | 514/729 |
| 5,545,665 A | 8/1996 | Burk | 514/530 |
| 5,607,978 A | 3/1997 | Woodward et al. | 514/646 |
| 5,688,819 A | 11/1997 | Woodward et al. | 514/357 |
| 5,834,498 A | 11/1998 | Burk | 514/445 |

FOREIGN PATENT DOCUMENTS

| | | |
|---|---|---|
| FR | 2258372 | 8/1975 |
| GB | 1439511 | 6/1976 |
| JP | 50-71650 | 6/1975 |
| WO | WO 96/36599 A | 11/1996 |
| WO | WO 99/25358 A | 5/1999 |

OTHER PUBLICATIONS

Yu, et al., Synthesis of Prostaglandin $E_2$ Ethanolamide from Anandamide by Cyclooxygenase–2, *Journal of Biological Chem.*, vol. 272, No. 34, pp. 21181–21186 (1975).
Woodward, D. F. et al.: "Neutral Replacement of the Carboxylic Acid Group of Prostaglandin F2alpha Provides A Novel Series of Ocular Hypotensive Lipids with Pharmacological Activity Distinct Prostanoids." IOVS, (Mar. 15, 1998) vol. 39, No. 4, pp. S420. Meeting Info: Annual Meeting of the Association for Research In Vision and Opthamolgy, Fort Lauderdale, Florida, USA May 10–15, 1998 Association for Research In Vision and Opthamology, XP00104773;
Schaaf, Thomas K., et al.: "Synthesis and Biological Activity of Carboxyl–Terminus Modified Prostaglandin Analogs" J. Med. Chem. (1979), 22(11), 1340–6, XP002184770.
Bito L. Z., Biological Protection with Prostaglandins, M.M., et., Boca Raton, Fla., CRC Press Inc., 1985, pp. 231–252.
Bito L. Z., Applied Pharmacology in the Medical Treatment of Glaucomas, Drance, S.M. and Neufeld, A.H. eds., New York, Grune & Stratton, 1984, pp. 477–505.
Abramovitz et al., *J. Biol. Chem.*, 269:2632 (1994).
Meade et al., *J. Biol. Chem.*, 268: 6610–6614 (1993).
Ogletree et al., *J. Pharmacol Exp. Ther.*, 234: 435–441 (1985).
Chen et al., *Br. J. Pharmacol*, 116: 3035–3041 (1995).

*Primary Examiner*—Robert Gerstl
(74) *Attorney, Agent, or Firm*—Gabor L. Szekeres; Martin A. Voet; Carlos A. Fisher

(57) ABSTRACT

Compounds of Formula 1, where the symbols are as defined in the specification, are useful as ocular hypotensive agents but do not exert their activity through the FP prostaglandin receptor.

Formula 1

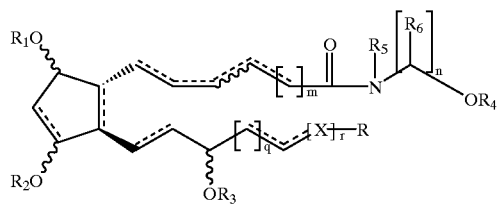

In particular the compound $PGF_{2\alpha}$ 1-ethanolamide, having the formula

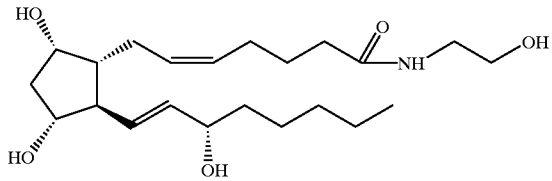

was discovered to be present in mammalian tissue as a naturally occurring substance, was synthesized in a substantially pure form and was found to be effective for lowering intraocular pressure in the mammalian eye, but not acting through the FP receptor through which many ocular hypotensive prostaglandins act.

34 Claims, 8 Drawing Sheets

OCULAR HYPOTENSIVE LIPIDS

BACKGROUND OF THE INVENTION

1. Field of the Invention

The present invention relates to ocular hypotensive lipids. More particularly the present invention relates to $PGF_{2\alpha}$ 1-ethanolamide and related compounds, and to pharmaceutical compositions containing these compounds, as well as methods for using the compounds to lower intraocular pressure in a mammal.

2. Brief Description of the Prior Art

The prior art is well aware of numerous ocular hypotensive agents which are used to treat various ocular hypertensive conditions, including primary and secondary glaucoma which represent a serious human health problem. Drugs used for treating ocular hypertension (glaucoma) include $\beta$-adrenoreceptor antagonists, and various prostaglandins. There is a substantial volume of scientific and patent literature pertaining to prostaglandins and to their use in the treatment of ocular hypertension. See for example Bito L. Z. *Biological Protection with Prostaglandins* Cohen, M. M., ed., Boca Raton. Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505.

U.S. Pat. No. 5,288,754 includes further citations to specific prior art directed to prostaglandins and related derivatives which are active as agents for reducing intraocular pressure in a mammal. U.S. Pat. No. 5,288,754 itself, describes "Polar C-1 Esters of Prostaglandins", including C-1 amides and C-1 substituted amides of the carboxylic acid compound known as $PGF_{2\alpha}$. Additional prostaglandin derivatives related to $PGF_{2\alpha}$ which have emerged in prior art research conducted in the research facilities of the corporate assignee of the present application and which show strong intraocular hypotensive activity, are shown below by formula and are identified by arbitrary numbers as "prior art compound no. 1" and "prior art compound no. 2". Prior art compound no. 1 is described in U.S. Pat. Nos. 5,352,708; 5,607,978 and 5,688,819, and prior art compound no. 2 is described in U.S. Pat. No. 5,545,665.

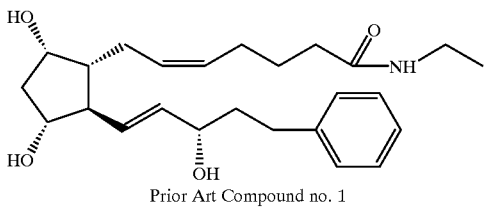

Prior Art Compound no. 1

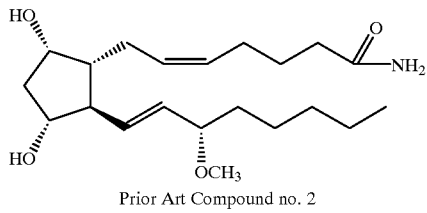

Prior Art Compound no. 2

The vast majority of ocular hypotensive agents which have a prostaglandin (or closely) related structure act through known "prostglandin" receptors. Particularly, the compound $PGF_{2\alpha}$ is known to exert its ocular hypotensive action through the receptor known as FP. By "FP receptor" is meant a human prostaglandin receptor as disclosed in Abramovitz et al., *J. Biol. Chem.* 269:2632 (1994), hereby incorporated by reference herein. The structure of $PGF_{2\alpha}$, including the numbering customarily used in the nomenclature of prostaglandin and related compounds, is shown below.

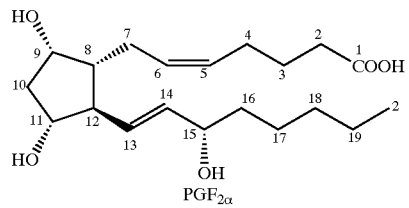

$PGF_{2\alpha}$

The present invention is directed to a class of compounds related to $PGF_{2\alpha}$ 1-ethanolamide, which suprisingly have been discovered, together with the prior art compound nos. 1 and 2, as agents having strong ocular hypotensive activity, but which do no exert their ocular hypotensive effects through the FP receptor, nor through any hitherto recognized prostaglandin receptor, such as DP, EP, $EP_2$, $EP_3$, $EP_4$, FP, IP and TP.

SUMMARY OF THE INVENTION

The present invention is directed to compounds of Formula 1 wherein the dashed lines represent absence of a bond, or a bond with the proviso that there are no two adjacent double bonds in the formula;

the wavy line attachments represent either alpha ($\alpha$, down) or beta ($\beta$, up) configuration, where the wavy lines are attached to a double bond they represent either Z (cis) or E (trans) configuration;

the hatched lines indicate alpha ($\alpha$) configuration and solid triangles indicate beta ($\beta$) configuration;

m is an integer having the values of 0 to 5;

n is an integer having the values 1–6, with the proviso that the compound represented by the formula is not $PGF_{2\alpha}$ 1-ethanolamide;

q and r each independently are integers having the value of 0 to 6;

X is $CH_2$, O or S with the proviso that when X is O or S then the dashed line adjacent to X represents absence of a bond;

R is $CH_3$, phenyl, furyl, thienyl, cycloalkyl of 3 to 8 carbons, or phenyl furyl or thienyl itself substituted with one or two substituents selected from the group consisting of F, Cl, Br, alkyl of 1 to 6 carbons, $NO_2$, CN, COOH and COOalkyl where alkyl has 1 to 6 carbons;

$R_1$, $R_2$, $R_3$, and $R_4$ each independently represent H, a straight or branch-chained alkanoyl group having 1 to 6 carbons, benzoyl or lower alkyl of 1 to 6 carbons;

$R_5$ is H or straight or branch-chained alkyl group having 1 to 6 carbons, and $R_6$ is H or straight or branch-chained alkyl of 1 to 4 carbons or a pharmaceutically acceptable salt of said compound, and said compounds being active to lower intraocular pressure in the eye of a mammal but do not exert their ocular hypotensive activity through the FP prostaglandin receptor, nor through any hitherto recognized prostaglandin receptor.

Formula 1

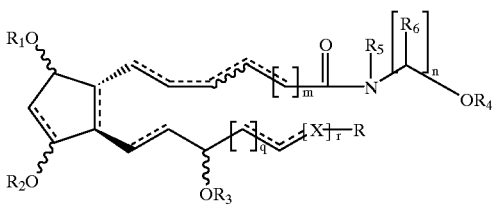

The present invention is also directed to isolated substantially pure $PGF_{2\alpha}$ 1-ethanolamide, which has surprisingly been discovered to be present in certain biological systems as a naturally occurring substance. Further, the present invention is directed to pharmaceutical compositions containing as an active ingredient $PGF_{2\alpha}$ 1-ethanolamide and/or one or more of the compounds in accordance with Formula 1, and to the process of treating a mammal, including a human, in need of such treatment with an effective amount of a pharmaceutical composition containing as active ingredient $PGF_{2\alpha}$ 1-ethanolamide and/or one or more of the compounds in accordance with Formula 1, for the purpose of lowering intraocular pressure.

DETAILED DESCRIPTION OF THE INVENTION

Figure 1:
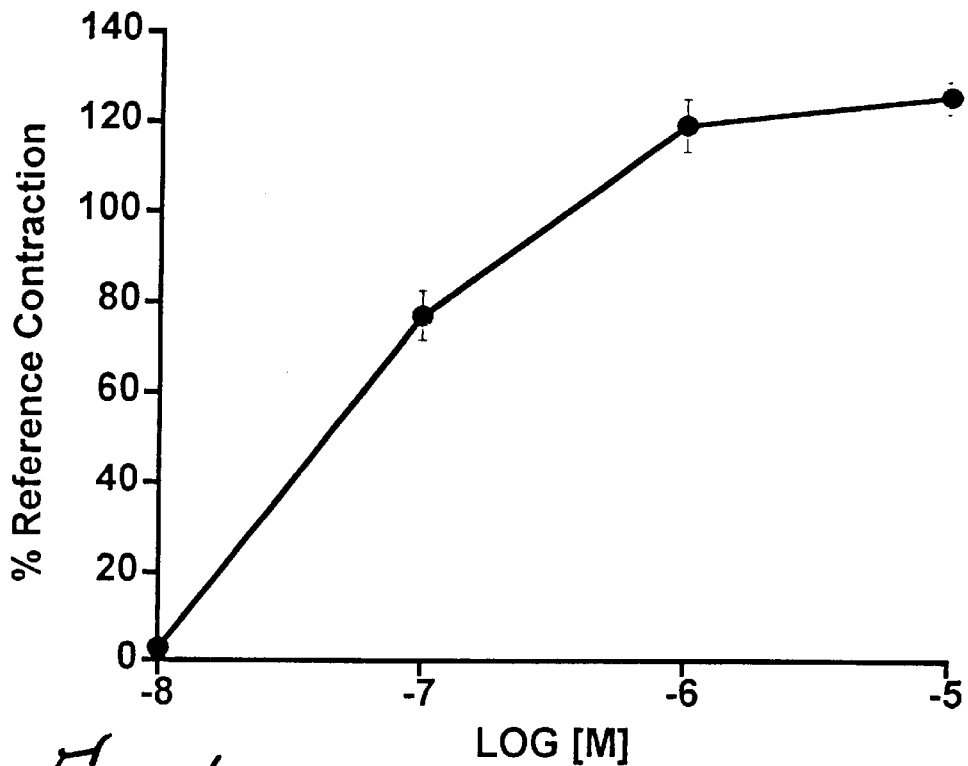
FIG. 1 is a graph showing the effect of graded doses of $PGF_{2\alpha}$ 1-ethanolamide on feline iris sphincter smooth muscle. Points are mean values±SEM; n=4.

Surprisingly it was discovered in connection with the present invention that $PGF_{2\alpha}$ 1-ethanolamide is a naturally occurring substance that may be formed from anandamide, a natural cannabinomimetic, by recombinant COX-2 and PGF synthase. It is known that COX-2 (cyclo-oxygenase-2) is a prostaglandin endoperoxide synthase which is inducible and not constitutively present in tissues (see Meade et al. (1993) J. Biol. Chem. 268: 6610–6614.) Since COX-2 would not be expected to be present in non-stimulated tissues, the finding in connection with the present invention that substantial quantities of $PGF_{2\alpha}$ ethanolamide were formed following anandamide administration to naive mice is unexpected. Moreover, surprisingly $PGF_{2\alpha}$ ethanolamide was also detected in mice that did not receive anandamide, suggesting that $PGF_{2\alpha}$ 1-ethanolamide is constitutive and may behave as an endogenously synthesized hormone.

In accordance with the invention $PGF_{2\alpha}$ 1-ethanolamide was synthesized to provide this substance in an isolated and substantially pure form, and to enable the formulation of pharmaceutical compositions containing this substance. The synthesis of $PGF_{2\alpha}$ ethanolamide also enables the synthesis of all compounds within the scope of Formula 1 with only such modifications in the synthetic process which are readily available to the practicing organic chemist, and particularly to the chemist practicing in the field of prostaglandin and related chemistry. Thus, the present invention encompasses the compounds of Formula 1.

Formula 1a

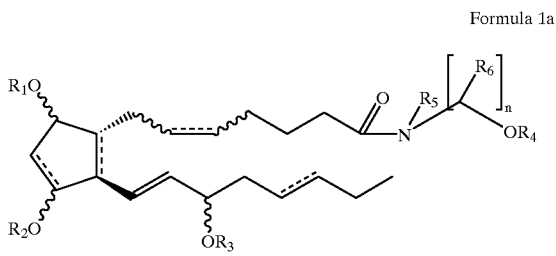

Preferred compounds within the scope of the invention are shown in Formula 1a, and particularly preferred are compounds within the scope of Formula 1a where the dashed lines between carbons 10 and 11, 8 and 12 and 17 and 18 represent absence of a bond, and between carbons 5 and 6 represent a bond. Further, as far as the substitution of the hydroxyl functions of the compounds of Formula 1a or of Formula 1 are concerned ($R_1$ through $R_4$ groups), compounds are presently preferred where one or more of the hydroxyl functions is not esterified nor alkylated (one or more of $R_1$ through $R_4$ is H), or when esterified the esterifying group is alkanoyl having 1 through 6 carbons (formyl, acetyl, propanoyl, butanoyl, pentanoyl, hexanoyl, or any branched chain alkanoyl of 3 to 6 carbons). As far as the substituent designated $R_5$ in Formula 1a or in Formula 1 is concerned, compounds are preferred where $R_5$ is H, or lower alkyl of 1 to 3 carbons, more preferably H. $R_6$ is preferably H or lower alkyl of 1 to 3 carbons, more preferably H, and n is preferably 2.

Referring still to Formula 1a and Formula 1, the configuration of the $OR_1$, $OR_2$ and $OR_3$ groups is preferably alpha (C-9, C-11 and C-15 α), and the configuration of the 5-6 double bond is preferably Z (cis).

The most preferred compounds in accordance with the present invention are $PGF_{2\alpha}$ 1-ethanolamide and its acylated or alkylated derivatives, shown in Formula 2, where $R_1$ through $R_4$ are defined as in connection with Formula 1, but the acylated derivatives are more preferred than the alkylated ones.

Formula 2

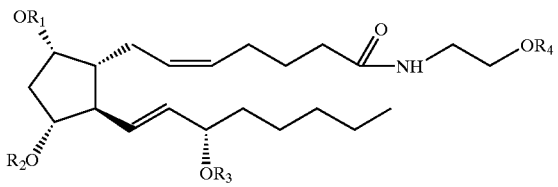

$PGF_{2\alpha}$ 1-ethanolamide = $R_1 = R_2 = R_3 = R_4 = H$

The synthesis of the compounds of the invention is illustrated by the synthesis of $PGF_{2\alpha}$ 1-ethanolamide shown in Reaction Scheme 1, and also disclosed below in experimental detail. Referring now to the reaction scheme, the commercially available triethanolamine (tromethamine) salt of the carboxylic acid $PGF_{2\alpha}$ is treated with acid to provide the free carboxylic acid. The free carboxylic acid $PGF_{2\alpha}$ is converted to the methyl ester by treatment with a methylating agent (preferably methyl iodide) in the presence of an acid acceptor (preferably 1,8-diazabicyclo[5.4.0]undec-7-ene) to provide $PGF_{2\alpha}$ methyl ester. $PGF_{2\alpha}$ methyl ester is thereafter treated with ethanolamine to provide $PGF_{2\alpha}$ 1-ethanolamide. Thus, the entire "amide" moiety is introduced into the molecule in the reaction between $PGF_{2\alpha}$ methyl ester and a hydroxyalkylamine derivative of Formula 3, where $R_5$ and $R_6$ and n are defined as in connection with Formula 1, and where Formula 3 represents ethanolamine when $R_5$, $R_6$ are H and n is 2. The hydroxylalkylamines of Formula 3 are available from the chemical literature and are well within the skill of the practicing organic chemist. Compounds where in Formula 1 one or more of the dashed lines represent a bond, and/or where the configuration of the hydroxyl groups, or the configuration of the substituents about one or more double bonds is different than in $PGF_{2\alpha}$ 1-ethanolamide, can be obtained by reactions analogous to the ones shown in Reaction Scheme 1, however starting with the prostaglandin derivative C-1 carboxylic acid of the appropriate corresponding structure and stereochemistry. These starting compounds are available in accordance with the chemical literature and are within the skill of the practicing organic chemist. Compounds where in Formula 1 one or more of the $R_1$ through $R_4$ groups is other than H, that is, compounds where one or more of the C-9, C-11, C-15 and the hydroxyl group of the hydroxyalkyl moiety in the amide portion are esterified, or alkylated can be obtained by esterification or alkylation reactions from the "free hydroxyl" compounds. Generally speaking, the modifications of the α and ω side chains of the compounds of Formula 1 as defined in connection with that formula, are within the skill of the practicing synthetic organic chemist in accordance with or in analogy to the disclosures in U.S. Pat. Nos. 5,545,665; 5,834,498 and 5,352,708 the specifications of which are expressly incorporated herein by reference.

Reaction Scheme 1

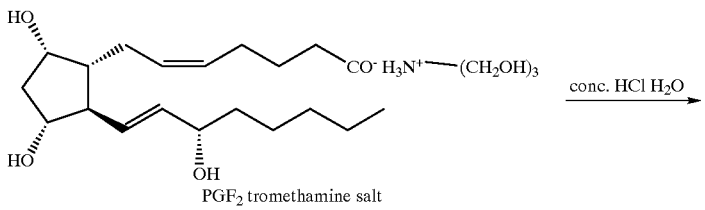

$PGF_2$ tromethamine salt

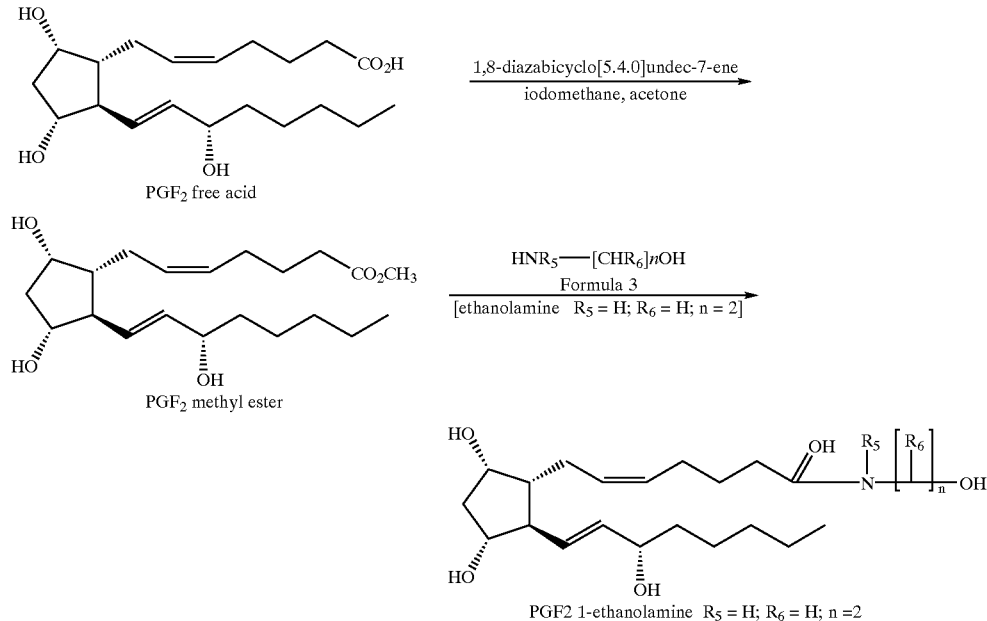

PGF₂ free acid

PGF₂ methyl ester

PGF2 1-ethanolamine R₅ = H; R₆ = H; n = 2

Biological Activity

The compounds of the invention are unique in that they are potent ocular hypotensive agents which nevertheless do not act through the FP receptor. This is demonstrated in a number of assay procedures which are well accepted in the art for establishing intraocular hypotensive activity as well as for determining the receptor through which the compounds act. The intraocular hypotensive activity of $PGF_{2\alpha}$ 1-ethanolamine and its virtual inertness in a number of assays which probe for activity of the FP or other known prostaglandin receptors are particularly striking and surprising when the biological profile of this compound is compared with the "parent" compound $PGF_{2\alpha}$.

Description of the biological assays, and results in the assays is provided below.

Methods

Isolated Tissue Studies

Smooth muscle tension of isolated tissues was measured isometrically with force displacement transducers (Grass FT-03) and recorded on Grass Polygraphs (Models 7G and 79E). The organ baths contained Krebs solution maintained at 37° C. and gassed with 95% $O_2$/5% $CO_2$ to give a pH of 7.4. The Krebs solution had the following composition (mM): NaCl, 118.0; KCl, 4.7; $KH_2PO_4$, 1.2; $CaCl_2$, 1.9; $MgSO_4$, 1.18; $NaHCO_3$, 25.0; glucose, 11.7; indomethacin, 0.001.

(a) Cat Iris

Adult domestic cats were sacrificed by intravenous overdose of sodium pentobarbital (Anthony, Arcadia, Calif.). The eyes were enucleated immediately and placed on ice. The iris sphincter muscle was mounted vertically under 50 to 100 mg tension in a jacketed 10 ml organ bath. A 60 min stabilization period was allowed before commencing each experiment. Activity was determined as contractile responses. Compounds were added cumulatively to the organ bath and at least 30 min was allowed for recovery, after complete wash-out, and return to baseline tension. The response to $10^{-7}$M $PGF_{2\alpha}$ was determined at the beginning and end of each experiment and between dose-response curves as a reference. No more than two compounds were tested in each tissue.

(b) Rat Aorta

Adult Sprague Dawley rats weighing 180–220 grams were anesthetized by $CO_2$ inhalation and then decapitated and exsanguinated. The thoracic aorta was removed and cleaned of any adhering tissue. The lumen was flushed to remove any blood. The aorta was dissected into three small segments of 5–8 mm length. Each segment was mounted under 2 g of tension in a jacketed 10 ml organ bath with the aid of two wire hooks placed through the lumen of the vessel. This arrangement allowed for measurement of contraction forces developed by the circular smooth muscle. The tissues were allowed to equilibrate for 1 hour before compounds were added cumulatively to the organ baths. The response to $10^{-7}$ M U-46619 (a thromboxane mimetic) was determined at the beginning and end of each experiment as a reference. A 30–45 minute recovery period was allowed after complete wash-out of drug. Only one test compound was examined in each tissue.

(c) Chick Ileum

The chick ileum is an $EP_3$ receptor preparation. Portions of the chick ileum of 1.5 cm length were suspended under 1 g of tension. After a one hour equilibration period, a standard dose-response curve for $PGE_2$ was obtained in a non-cumulative fashion with 30 minute wash-out periods between individual doses. Subsequently, test compound was added non-cumulatively. A maximal dose of $PGE_2$ ($10^{-6}$ M) was finally given to serve as a second reference standard. Contractile activity at each concentration was then calculated as a % of the maximal $PGE_2$ response reached at a $10^{-6}$ M concentration.

(d) Guinea Pig Ileum

The guinea pig ileum is an $EP_1$ receptor preparation. An approximately 1.5 cm segment of guinea pig ileum was suspended in a jacketed organ bath under 1 g tension. Following a 1 hr equilibration period, a wash-out dose response curve for $PGE_2$ was obtained. 30 min wash-out periods were allowed between doses. A dose response curve was then generated for $PGF_{2\alpha}$ 1-ethanolamide in an identical manner. A final administration of $PGE_2$ $10^{-6}$ M was given as a reference. Data were expressed as % maximal of the $PGE_2$ response.

(e) Guinea Pig Vas Deferens

Activity at the prostaglandin-sensitive $EP_3$ receptor subtype was also determined by the ability of prostanoids to inhibit the smooth muscle twitch response stimulated by an electrical current in the isolated guinea pig vas deferens. 1.5 cm portions of the guinea pig vas deferens were suspended under 1 g initial tension and allowed to equilibrate for at least 30 minutes. Tissues were then subjected to stimulation every 30 seconds by 20 volt electrical pulses. After stabilization of the twitch response, a standard dose response curve to $PGE_2$ was performed in a cumulative fashion. Test compounds were then evaluated by performing a cumulative dose response curve. Tissues were washed-out and allowed to equilibrate for 1 hr between compounds. $PGE_2$ was once again evaluated at the conclusion of the experiment as a standard reference. Activity was calculated as the percent inhibition of the height of the muscle twitch response.

(f) Rabbit Jugular Vein

New Zealand albino rabbit of either sex, weighing 2–4 kg, were injected with 1000 U heparin into the marginal ear vein and then sacrificed by $CO_2$ gas. The external jugular veins were cleared of fat and adherent connective tissue and removed. The veins were transected and each ring of 3–4 mm length was suspended between two metal hooks in a jacketed organ bath. The tissues were equilibrated for 1 hr under 0.75 g tension, which was readjusted as the tissues relaxed. Single doses of histamine, $10^{-5}$ M then $2-3\times10^{-6}$ M, with washing after each dose, were given to contract the tissue and establish responsiveness. The TP-receptor antagonist SQ29548, (Ogletree et al. (1985) J. Pharmacol. Exp. Ther. 234 435–441) at ($10^{-6}$ M), was applied for 5 min and then histamine $2-3\times10^{-6}$ M was added to elicit the contractile response. After 30 min of pretreatment with the histamine, the relaxant response was tested by adding cumulative doses of the test compounds with $10^{-8}$ M to $10^{-7}$ M $PGE_2$ at the end of each dose-response curve as a reference. A recovery period of 30–50 min was allowed after wash-out of the tissues. Relaxant activity was calculated as % of the control tone elicited by histamine.

(g) Human Platelets

Prostanoid activity at the DP-, TP- and IP-receptor types was determined by an ability to cause aggregation (TP-receptor activity) or to inhibit ADP-induced aggregation of human platelets in vitro (DP- and IP-receptor activity). Fresh whole blood was obtained from consenting healthy human volunteers and mixed with acid citrate-dextrose (ACD). The blood was centrifuged at 1000 rpm for 15–20 minutes to obtain platelet rich plasma (PRP). 4.5 µl of prostanoid or vehicle was added to 450 µl of PRP and incubated for 2 minutes at 37° C. in a Payton aggregometer and observed for any aggregatory activity. $2\times10^{-5}$ M ADP (final concentration) was then added to induce full aggregation. Inhibition of aggregation was calculated as the percentage difference between aggregation evoked by $2\times10^{-5}$ M ADP in the absence and presence of drug. Aggregatory activity was calculated as the percent aggregation induced by the prostanoid relative to the aggregation induced by $2\times10^{-5}$ M ADP. Standard aggregatory responses to $2\times10^{-5}$ M ADP alone were performed at the beginning and end of each experiment.

(h) CRL 1497 Cells: $Ca^{2+}$ Signal.

Human CRL 1497 cells were plated in culture flasks and fed Dulbecco's modified Eagle's medium (DMEM) containing 10% fetal calf serum, 2 mM 1-glutamine, and 0.05 mg/ml gentacin (all purchased from Gibco, Grand Island, N.Y.). Cell cultures were maintained in a humidified atmosphere of 95% air, 5% $CO_2$ and grown to confluency. Cells were removed from the culture flasks by approximately 1 min treatment with trypsin 0.05%/0.53 mM EDTA in Hanks Balanced Salt Solution (HBSS, Gibco, Grand Island, N.Y.) at 37° C. Proteolytic activity was arrested by adding 5 ml of 10% fetal bovine serum in DMEM. The cells were consecutively washed in Hank's BSS and medium containing 140 mM NaCl, 50 mM KCl, 1 mM $MgCl_2$, 1.5 mM $CaCl_2$, 10 mM HEPES: TRIS, 5 mM glucose, 5 mM Na pyruvate, 0.1% bovine serum albumin at pH 7.4: Centrifugation for the washes was performed for 15 minutes at 200 g at room temperature. Cells were counted, resuspended in the above medium and incubated with $2\times10^{-6}$ M Fura 2/acetoxymethyl ester in a shaking water bath for 30 minutes at 37° C. The cells were subsequently washed in medium as above and resuspended at a concentration of $2\times10^6$ cells $ml^{-1}$. Aliquots of 0.5 ml cell suspension were then added to autocap microtubes to provide $10^6$ cells per experimental determination of intracellular free $Ca^{2+}$ concentration ($[Ca^{2+}]_i$).

Fluorescence was measured in a Perkin-Elmer LS-5 fluorescence spectrophotometer at excitation and emission wavelengths of 340 and 492 nm, respectively, with both slits at 10 nm. For each experimental determination $10^6$ cells were washed (200×g for 5 min) and suspended in a 2 ml cuvette with buffer containing 120 mM NaCl, 6 mM KCl, 1 mM $MgSO_4$, 1.5 mM $CaCl_2$, 20 mM HEPES, 1 mg $ml^{-1}$ glucose and 1 mg $ml^{-1}$ Na pyruvate. Stirring was achieved by an overhead-mounted, paddle stirrer with the temperature maintained at 37° C. The cells were lysed with digitonin (10 µl of 100 mg $ml^{-1}$ DMSO) to obtain $f_{max}$. EGTA (100 mM) and sufficient 10N NaOH to adjust the pH to 8.5 were then successively added to obtain $f_{min}$.

(i) Recombinant Cat and Human FP Receptor; Stable Transfectants

HEK-293 cells were grown in DMEM with 10% fetal bovine serum (FBS), 250 µg $ml^{-1}$ G418 (Life Technologies) and 200 µg $ml^{-1}$ gentamicin or penicillin/streptomycin. Selection of stable transfectants was achieved with 200 µg $ml^{-1}$ hygromycin, the optimal concentration being determined by hygromycin kill curve studies. For transfection, the cells were grown to 50–60% confluency on 10 cm plates. The plasmid pCEP4 incorporating cDNA inserts for the human FP receptor (20 µg) was added to 500 µl of 250 mM $CaCl_2$. HEPES buffered saline×2 (2×HBSS, 280 mM NaCl, 20 mM HEPES acid, 1.5 mM $Na_2HPO_4$, pH 7.05–7.12) was then added dropwise to a total of 500 µl, with continuous vortexing at room temperature. After 30 min, 9 ml DMEM were added to the mixture. The DNA/DMEM/calcium phosphate mixture was then added to the cells, which had been previously rinsed with 10 ml phosphate buffered saline (PBS). The cells were then incubated for 5 h. at 37° C. in humidified 95% air/5% $CO_2$. The calcium phosphate solution was then removed and the cells were treated with 10% glycerol in DMEM for 2 min. The glycerol solution was then replaced by DMEM with 10% fetal bovine serum (FBS). The cells were incubated overnight and the medium was replaced by DMEM/10% FBS containing 250 µg $ml^{-1}$ G418 and penicillin/streptomycin. The following day hygromycin B was added to a final concentration of 200 µg $ml^{-1}$.

Ten days after transfection, hygromycin B resistant clones were individually selected and transferred to a separate well on a 24 well plate. At confluence each clone was transferred to one well of a 6 well plate, and then expanded in a 10 cm dish. Cells were maintained under continuous hygromycin selection until use. The stable cat FP receptor transfectants were similarly prepared using lipofectamine. Again cells were grown to 50–60% confluency on 10 cm plates and the plasmid pCEP4, incorporating cDNA inserts for the feline FP receptor, was transfected using lipofectin. Hygromycin B selection was started 48 hr post-transfection. Eight days after transfection, hygromycin B resistant clones were selected and transferred to 24 well plates. $Ca^{2+}$ signaling studies on recombinant cat and human FP receptors were performed in an identical manner to that described for the CRL 1497 cell studies.

(j) Inositol Phosphate Formation

Receptor-mediated phosphoinositide (PI) hydrolysis was determined by measuring the accumulation of total inositol phosphates (IP) in cells preincubated with $^3$H-myoinositol. Stable cell lines of HEK 293 cells expressing human or cat FP receptors were plated in 10 cm dishes ($10^6$ cells per dish in DMEM with 10% FBS). The following day, the cells were incubated with 18 $\mu$Ci myo-[2 $^3$H] inositol (Amersham; 10–20 $\mu$Ci mmol$^{-1}$) in 6 ml of DMEM with 10% FBS for 24 hours at 37° C. The cells were then rinsed twice with phosphate buffered saline (PBS), incubated for 5 min with 1 ml of trypsin-EDTA, and suspended in 10 ml DMEM containing 25 mM HEPES buffer. Cells were pelleted at 1000 rpm and resuspended in DMEM/25 mM HEPES containing 10 mM LiCl for 10 minutes. Aliquots of 200 $\mu$l cell suspension were incubated with 50 $\mu$l drug for 30 minutes at 37° C. (duplicate determination), and agonist stimulation was terminated with a 750 $\mu$l mixture of chloroform:methanol:4N HCl (100:200:2), followed by addition of 250 $\mu$l of chloroform and 0.5 N HCl for extraction of inositol phosphates. A 750 $\mu$l volume of the aqueous layer was loaded on columns packed with 0.5 ml of Dowex AG 1-X8 anion-exchange resin (formate form, 100–200 mesh; BioRad) to separate radiolabeled components. The elution procedure consisted of three 3 ml washes with 5 mM inositol, then two elutions with 750 $\mu$l of 1.3 M ammonium formate with 0.1 M formic acid. The eluate was mixed with 10 ml Aquasol scintillation fluid (Packard Instrument Co.) and total [$^3$H] inositol phosphates was determined by a liquid scintillation counter.

(k) Radioligand Binding

Plasma membrane preparations of HEK 293 cells stably transfected with the human or feline FP receptor were obtained as follows. Cells washed with TME buffer were scraped from the bottom of the flasks and homogenized for 30 sec using a Brinkman PT 10/35 polytron. TME buffer was added as necessary to achieve a 40 ml volume in the centrifuge tubes. TME is comprised of 100 mM TRIS base, 20 mM Mg Cl$_2$, 2 m EDTA; physiological pH is achieved by adding 10 N HCl. The cell homogenate was centrifuged at 19,000 rpm for 20 min at 4–6° C. using a Beckman Ti-60 rotor. The pellet was then resuspended in TME buffer to provide a final protein concentration of 1 mg/ml, as determined by Biorad assay. Radioligand binding assays were performed in a 200 $\mu$l volume.

The binding of [$^3$H](N) 17-phenyl PGF$_{2\alpha}$ (specific activity 85 Ci/mmol) was determined in duplicate and experiments were replicated three times. Incubations were for 60 min at 25° C. and were terminated by the addition of 4 ml of ice-cold 50 mM TRIS-HCl followed by rapid filtration through Whatman GF/B filters and three additional 4 ml washes in a cell harvester (Brandel). Competition studies were performed using a final concentration of 5 nM [$^3$H](N) 17-phenyl PGF$_{2\alpha}$ and non-specific binding was determined with $10^{-5}$ M unlabelled 17-phenyl PGF$_{2\alpha}$.

(l) Intraocular Pressure (IOP)

Intraocular pressure studies in dogs involved pneumatonometry performed in conscious, Beagle dogs of both sexes (10–15 kg). The animals remained conscious throughout the study and were gently restrained by hand. Drugs were administered topically to one eye as a 25 $\mu$L volume drop, the other eye received 25 $\mu$L vehicle (0.1% polysorbate 80:10 mM TRIS) as a control. 0.1% proparacaine was used for corneal anesthesia during tonometry. Intraocular pressure was determined just before drug administration and at 2, 4 and 6 hr thereafter on each day of the 5 day study. Drug was administered immediately after the first IOP reading.

(m) Pupil Diameter

Dog pupil diameter was measured using an optistick (a mm ruler which included half-circle references of standard widths (mm) for reference. Gently restraining the dog by hand, pupil diameter was determined by matching a half-circle to the pupil in normal room light. In dogs with very dark pupils a specialized penlight was used, but only very briefly to avoid pupil constriction. Pupil diameter was measured at the same time as IOP and hyperemia.

(n) Ocular Surface Hyperemia

Ocular surface hyperemia was visually assessed and scored according to a system typically used clinically.

| Hyperemia Score | Assigned Value |
| --- | --- |
| <1 trace | 0.5 |
| 1 mild | 1 |
| moderate | 2 |
| severe | 3 |

Ocular surface hyperemia was evaluated at the same time points as intraocular pressure measurement. It should be noted that untreated dog eyes frequently have a pink/red tone. Thus, values of trace or even mild are not necessarily out of the normal range.

Results

The effects of Prostaglandin F$_{2\alpha}$ 1-ethanolamide on the feline iris sphincter are depicted in FIG. 1 and tabulated (Table 1). Prostaglandin F$_{2\alpha}$ 1-ethanolamide (PGF$_{2\alpha}$ 1-ethanolamide) produced dose dependent contraction of cat iris sphincter smooth muscle. An effective concentration (E.C.)$_{50}$ value of 58 nM was obtained. The data indicate a threshold concentration in the region of 10 nM.

Figure 2:
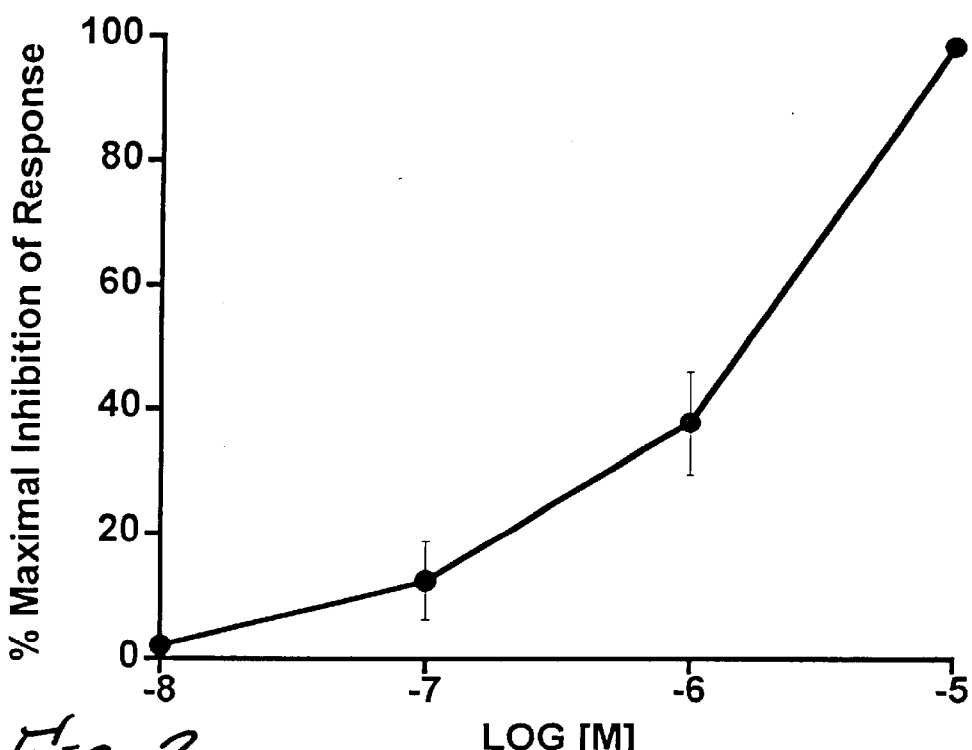
FIG. 2 is a graph showing the inhibitory effect of graded doses of $PGF_{2\alpha}$ 1-ethanolamide on field stimulated contraction of the isolated guinea pig vas deferens. Points are mean values±SEM; n=4.

Prostaglandin F$_{2\alpha}$ 1-ethanolamide was modestly effective in inhibiting field stimulation evoked contraction of the isolated guinea pig vas deferens preparation. The data are depicted in FIG. 2 and tabulated (Table 2).

Figure 3:
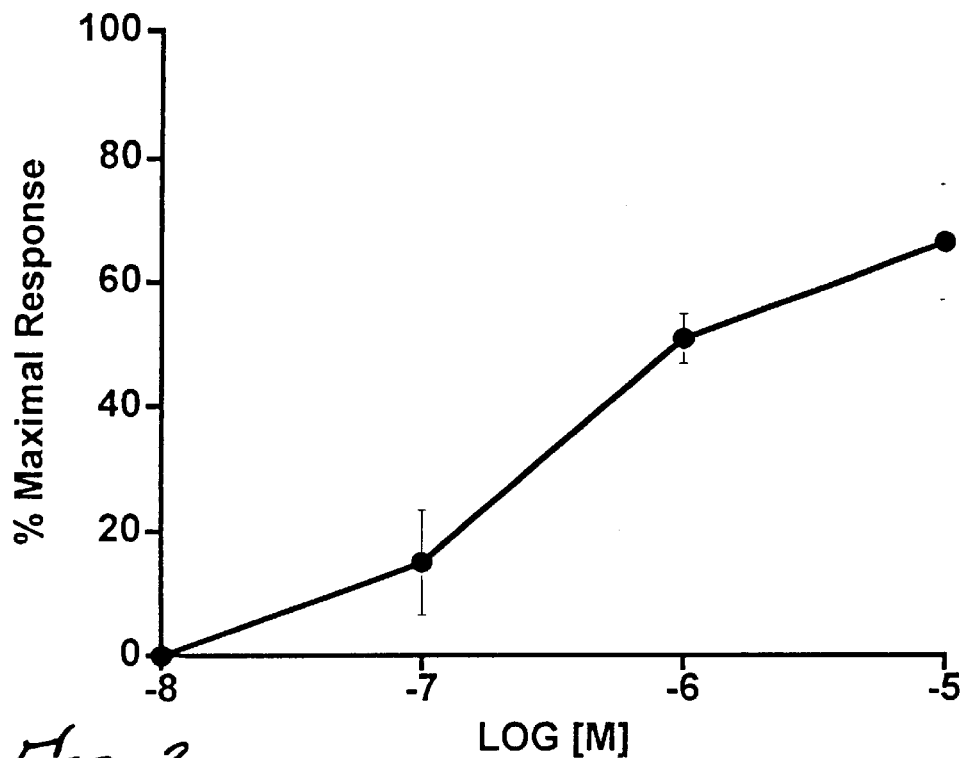
FIG. 3 is a graph showing the effect of graded doses of $PGF_{2\alpha}$ 1-ethanolamide on the isolated chick ileum. Points are mean values±SEM; n=4.
Figure 4:
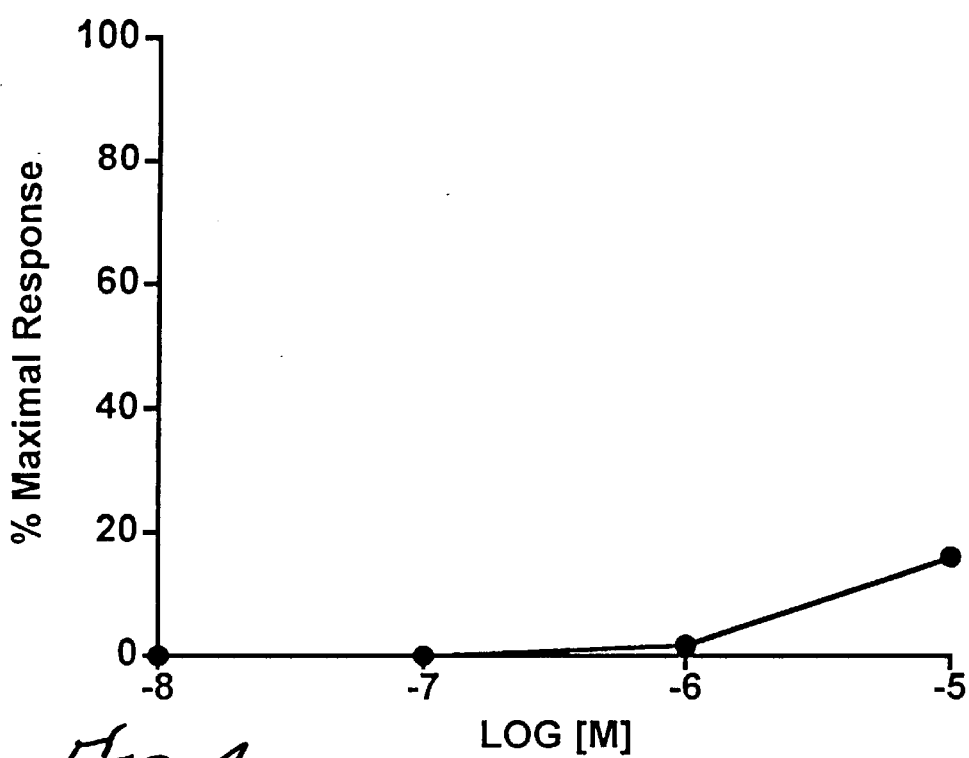
FIG. 4 is a graph showing the effect of graded doses of $PGF_{2\alpha}$ 1-ethanolamide on the isolated guinea pig ileum. Points are mean values±SEM; n=4.

FIG. 3 depicts the effect of PGF$_{2\alpha}$ 1-ethanolamide on the isolated chick ileum. Comparison of responses to the reference compound (prostaglandin E$_2$, $10^{-6}$ M) suggests that PGF$_{2\alpha}$ 1-ethanolamide may behave as a weak partial agonist. The data are listed in Table 3. PGF$_{2\alpha}$ 1-ethanolamide appeared less effective in the guinea pig ileum (FIG. 4; Table 4), which is reported to be an EP$_1$ receptor preparation.

Figure 5:
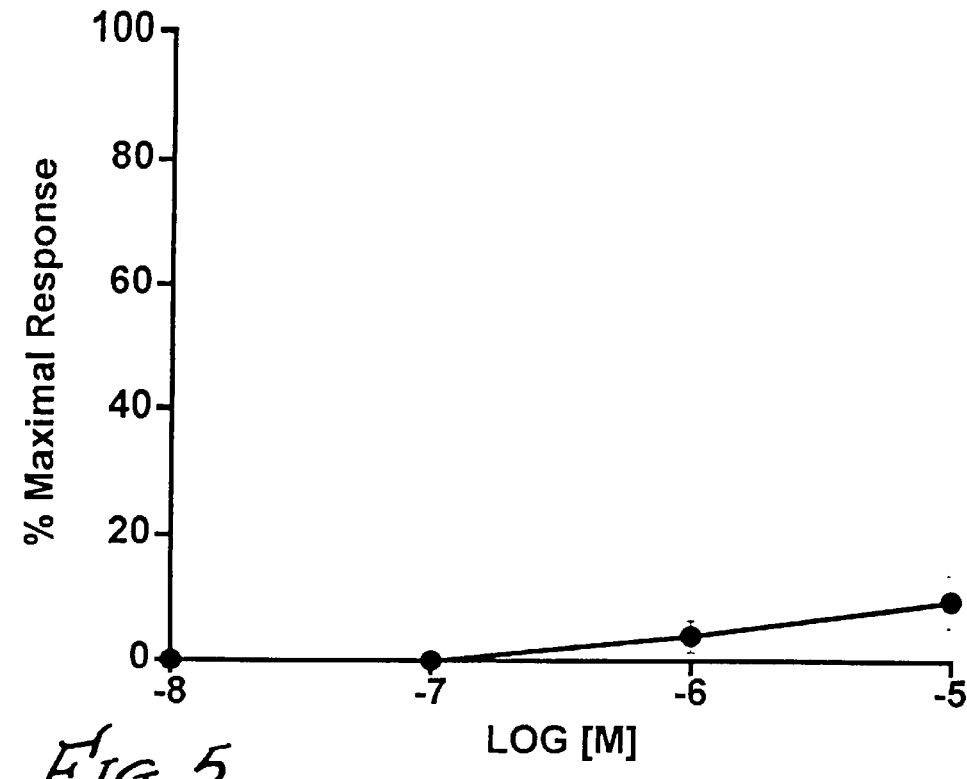
FIG. 5 is a graph showing the effect of graded doses of $PGF_{2\alpha}$ 1-ethanolamide on isolated rat aortic smooth muscle. Points are mean values±SEM; n=4.

The effects of graded doses of PGF$_{2\alpha}$ 1-ethanolamide on the isolated rat aorta are shown in FIG. 5 and Table 5. Residual activity occurred at high doses, $10^{-6}$ and $10^{-5}$ M. Since the rat aorta is a TP receptor preparation, activity at the TP receptor was further evaluated in terms of platelet aggregation. In addition, inhibition of ADP induced human platelet aggregation was determined to reveal any interaction at DP or IP receptors. No effect on platelets was apparent. The data are presented in Table 6; no graph is provided since absolutely no response occurred.

Figure 6:
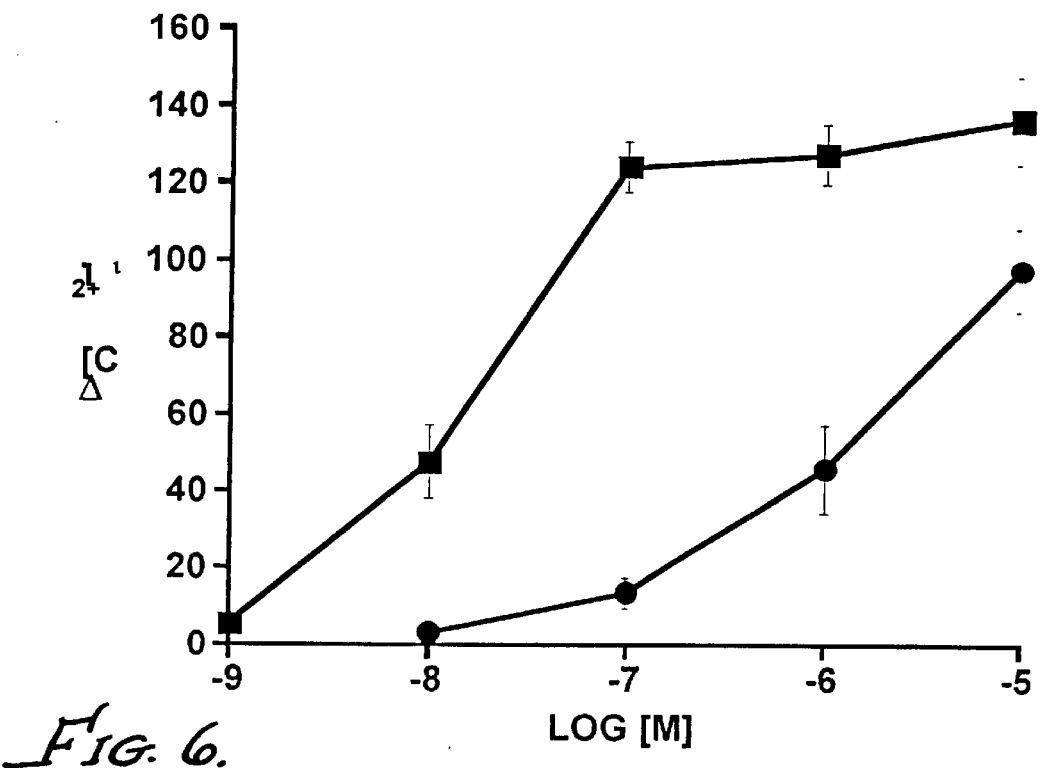
FIG. 6 is a graph showing the increases in intracellular $Ca^{2+}$ concentration $[Ca^{2+}]_i$ produced by graded doses of $PGF_{2\alpha}$ (■) and $PGF_{2\alpha}$ 1-ethanolamide (●) in CRL 1497 cells. Points are mean values±SEM; n=4.

The Ca$^{2+}$ signal produced by graded doses of Prostaglandin F$_{2\alpha}$ 1-ethanolamide in human dermal fibroblasts (CRL 1497 cells) is compared to that produce by Prostaglandin $F_{2\alpha}$ in FIG. 6. The data are also tabulated (Table 7). The E.C.$_{50}$ values obtained were 16 nM for PGF$_{2\alpha}$ and 1586 nM for PGF$_{2\alpha}$ 1-ethanolamide, indicating about a one hundred fold difference in potency at the human FP receptor.

Figure 7:
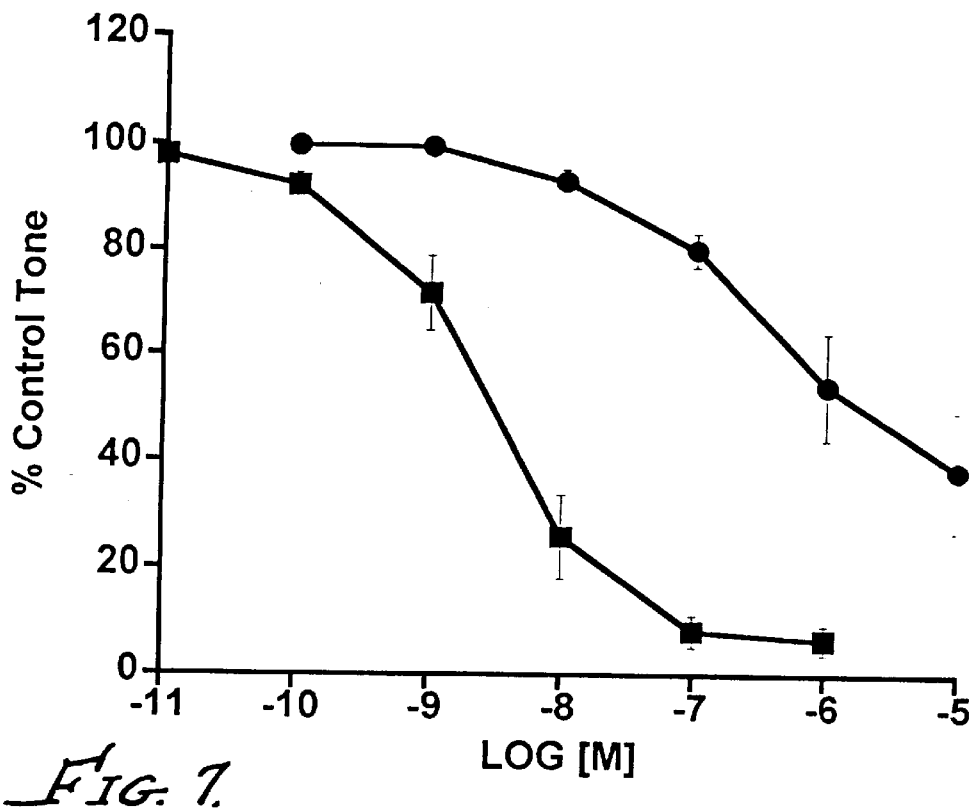
FIG. 7 is a graph showing the vasorelaxation effects of Prostaglandin $F_{2\alpha}$ 1-ethanolamide (●) and Prostaglandin $F_{2\alpha}$ (■) on the histamine precontracted rabbit jugular vein segment. Points are mean values±SEM; n=6 for $PGF_{2\alpha}$ 1-ethanolamide, n=7 for $PGF_{2\alpha}$.

Recent studies have shown that Prostaglandin $F_{2\alpha}$ can produce endothelium dependent, nitric oxide (NO) mediated vasorelaxation (Chen et al.(1995) Br. J. Pharmacol. 116: 3035–3041) Thus, the effects of PGF$_{2\alpha}$ 1-ethanolamide were compared to those of PGF$_{2\alpha}$ in producing endothelium dependent vasorelaxation of the histamine precontracted, isolated rabbit jugular vein segment. Although PGF$_{2\alpha}$ potently produced marked vasorelaxation, PGF$_{2\alpha}$ 1-ethanolamide exhibited relatively little activity (FIG. 7). The data are also tabulated (Table 8). The following E.C.$_{50}$ values were obtained for vasorelaxation of the precontracted rabbit jugular vein segment: PGF$_{2\alpha}$ 1-ethanolamide=2000 nM, PGF$_{2\alpha}$=5.3.

Figure 8:
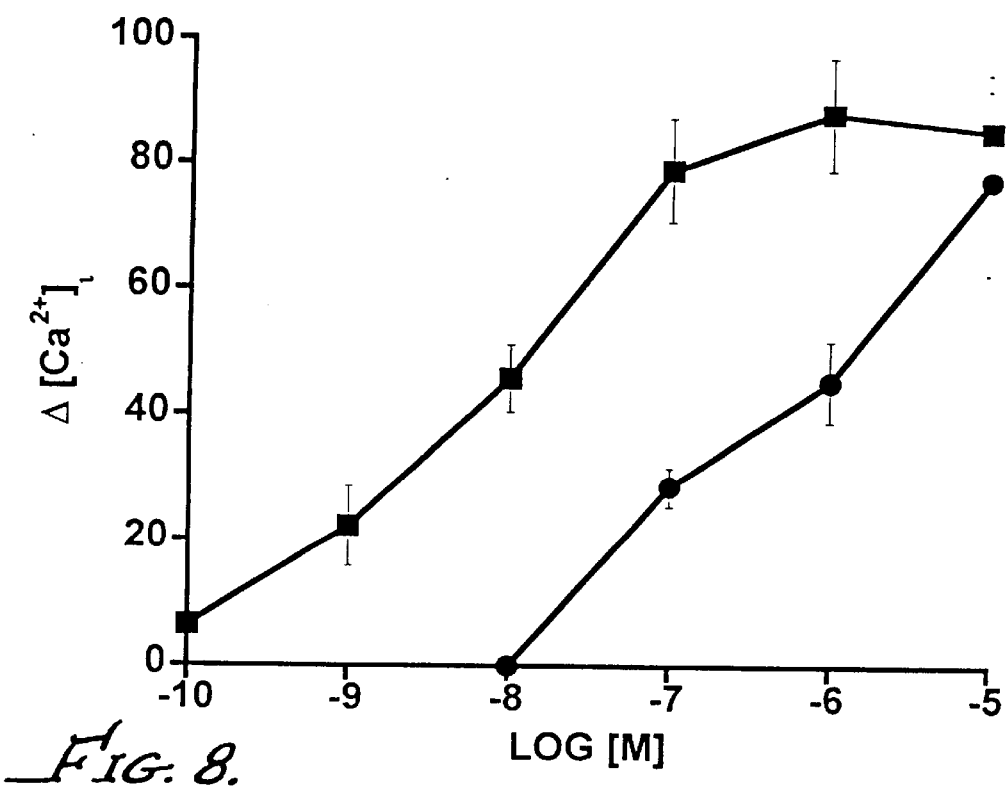
FIG. 8 is a graph showing the increases in intracellular $Ca^{2+}$ concentration $[Ca^{2+}]_i$ produced by graded doses of $PGF_{2\alpha}$ (■) and $PGF_{2\alpha}$ 1-ethanolamide (●) in HEK-293 cells stably transfected with the recombinant feline FP receptor. Points are mean values±SEM; n=3.

Since marked activity was observed for PGF$_{2\alpha}$ 1-ethanolamide in the cat iris sphincter preparation, its activity was compared to that of PGF$_{2\alpha}$ at the recombinant feline FP receptor. FIG. 8 compares the activity of PGF$_{2\alpha}$ 1-ethanolamide and PGF$_{2\alpha}$ in eliciting a Ca$^{2+}$ signal in HEK-293 cells stably transfected with the recombinant feline FP receptor. E.C.$_{50}$ values of 14 nM for PGF$_{2\alpha}$ and 1458 for PGF$_{2\alpha}$ 1-ethanolamide were obtained, indicating an approximately 100 fold difference in potency. The data are also tabulated (Table 9).

Figure 9:
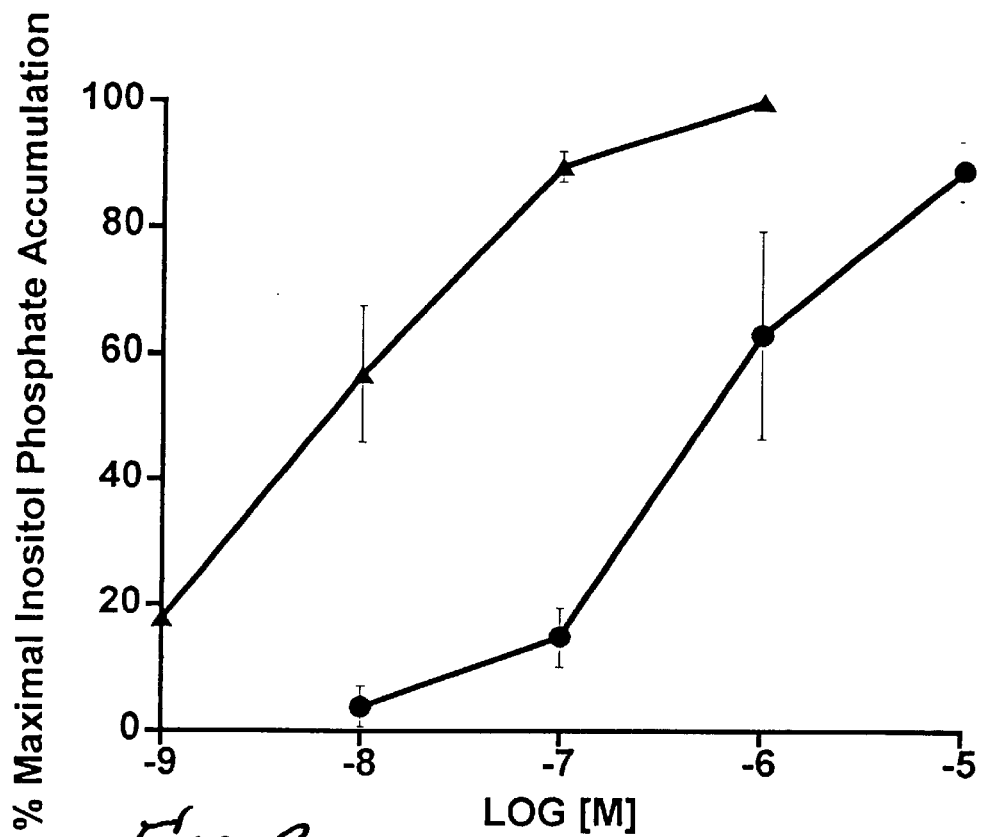
FIG. 9 is a graph showing the total inositol phosphate accumulation produced by graded doses of 17-phenyl prostaglandin $F_{2\alpha}$ (▲) and prostaglandin $F_{2\alpha}$ 1-ethanolamide (●) in HEK-293 cells stably transfected with the recombinant feline FP receptor. Values are mean±SEM. N=3.

The effects of PGF$_{2\alpha}$ 1-ethanolamide and 17-phenyl PGF$_{2\alpha}$ on total inositol phosphate accumulation in HEK-293 cells stably transfected with the recombinant feline FP receptor are depicted in FIG. 9. Again, a large separation in potency was apparent. E.C.50 values were 9 nM for 17-phenyl PGF$_{2\alpha}$ and 524 nM for PGF$_{2\alpha}$ 1-ethanolamide. The data are tabulated (Table 10).

Figure 10:
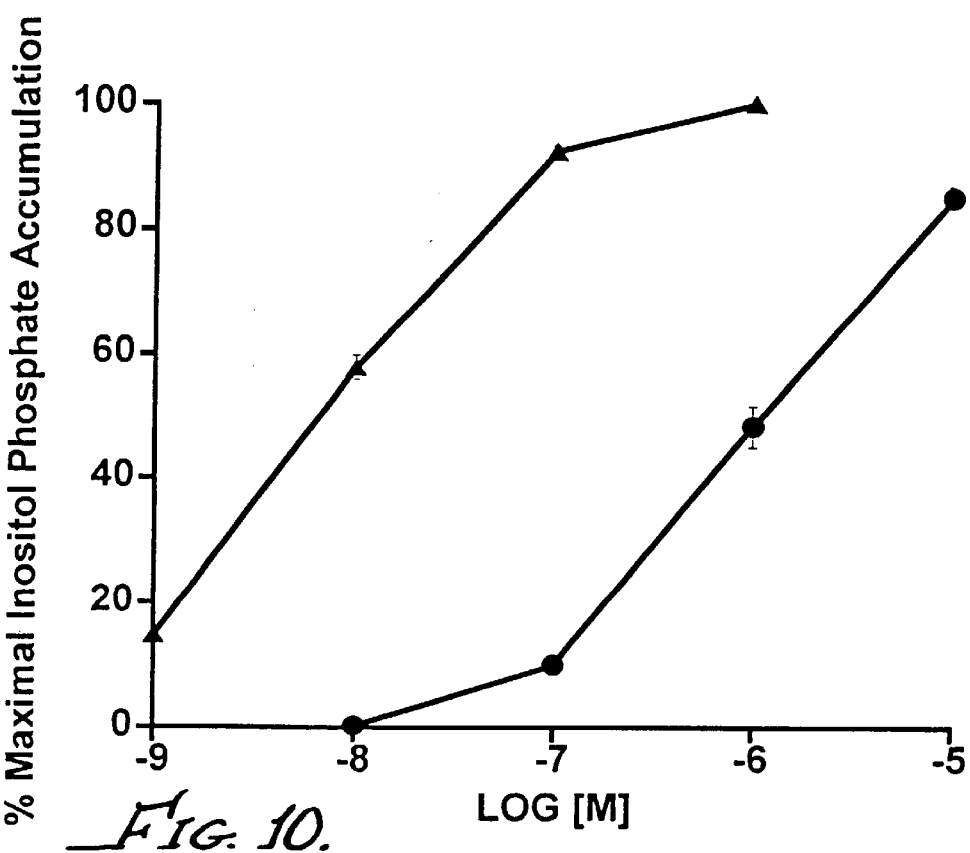
FIG. 10 is a graph showing the total inositol phosphate accumulation produced by graded doses of 17-phenyl prostaglandin $F_{2\alpha}$ (▲) and prostaglandin $F_{2\alpha}$ 1-ethanolamide (●) in HEK-293 cells stably transfected with the recombinant human FP receptor. Values are mean±SEM. n=3.

In addition, the effects of PGF$_{2\alpha}$ 1-ethanolamide and 17-phenyl PGF$_{2\alpha}$ on total inositol phosphate accumulation in HEK-293 cells stably transfected with the recombinant human FP receptor were examined. E.C.$_{50}$ values of 8 nM for 17-phenyl PGF$_{2\alpha}$ and 1003 nM were obtained. The data are presented in FIG. 10 and Table 11. Results were similar to those obtained for the recombinant feline FP receptor.

Figure 11:
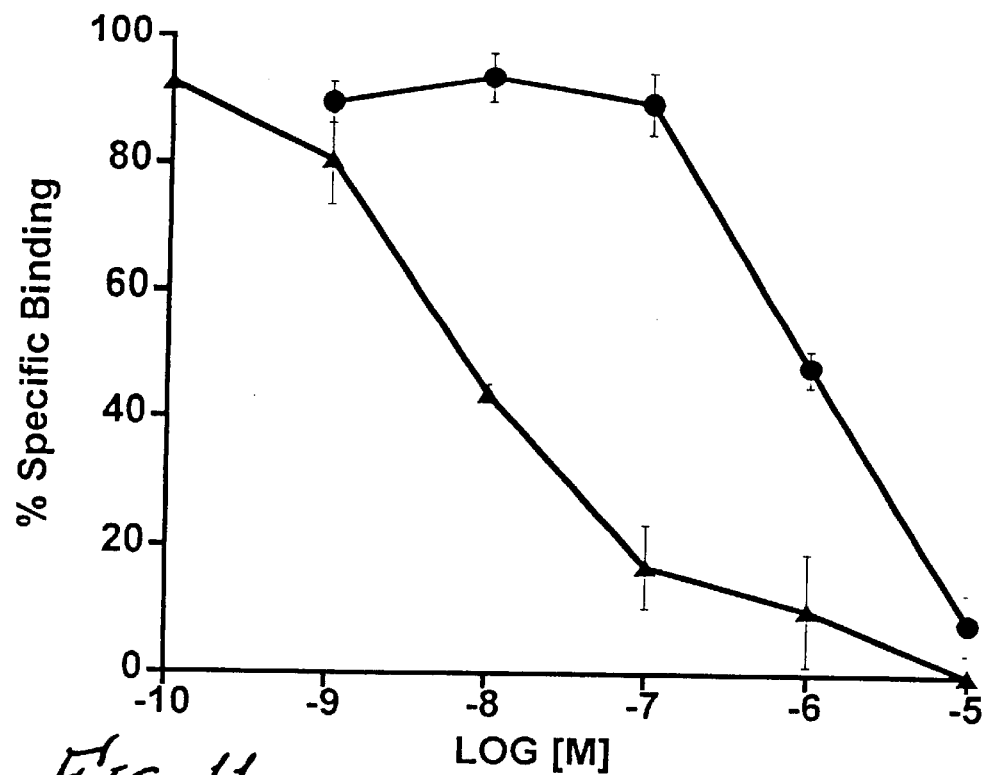
FIG. 11 is a graph showing the radioligand binding competition studies vs. 5 nM $^3$H-17-phenyl $PGF_{2\alpha}$ using HEK-293 cells stably transfected with the recombinant feline FP receptor. Competition afforded by unlabeled $PGF_{2\alpha}$ 1-ethanolamide (●) and unlabelled 17-phenyl $PGF_{2\alpha}$ (▲) is depicted. Points are mean values±SEM; n=3 of experiments performed in triplicate.
Figure 12:
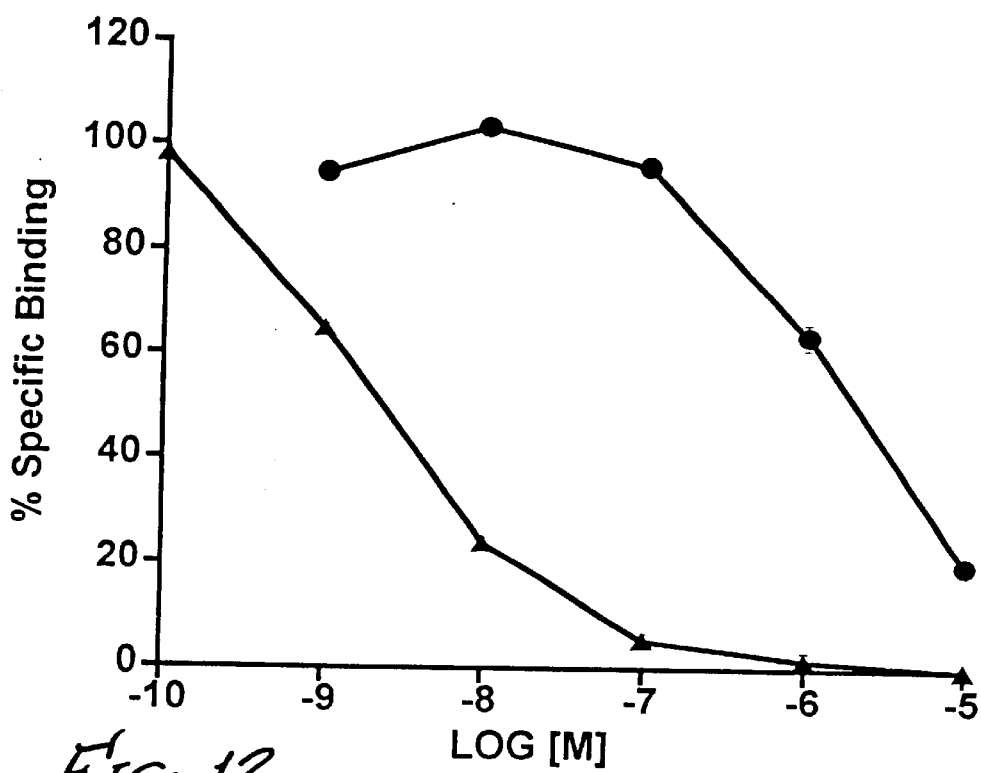
FIG. 12 is a graph showing the radioligand binding competition studies vs. 5 nM $^3$H-17-phenyl $PGF_{2\alpha}$ using HEK-293 cells stably transfected with the recombinant human FP receptor. Competition afforded by unlabeled $PGF_{2\alpha}$ 1-ethanolamide (●) and unlabelled 17-phenyl $PGF_{2\alpha}$ (▲) is depicted. Points are mean values±SEM; n=3 of experiments performed in triplicate.

Consistent with the functional studies employing stably transfected FP receptor preparations, PGF$_{2\alpha}$ 1-ethanolamide had relatively modest binding affinity for the FP receptor. Thus, PGF$_{2\alpha}$ 1-ethanolamide (prior art compound no. 1) had only weak affinity for the feline receptor, whereas 17-phenyl PGF$_{2\alpha}$ exhibited high affinity (FIG. 11; Table 12). The inhibitory concentration$_{50}$ (I.C.$_{50}$) for PGF$_{2\alpha}$ 1-ethanolamide obtained was 882 nM, compared to an I.C.$_{50}$ value of 43.5 nM for 17-phenyl PGF$_{2\alpha}$. Similar results were obtained for the recombinant human FP receptor: PGF$_{2\alpha}$ 1-ethanolamide I.C.$_{50}$ =2015 nM, 17-phenyl PGF$_{2\alpha}$ I.C.$_{50}$ =2.3 nM. These radioligand binding data are depicted in FIG. 12 and tabulated (Table 13).

Figure 13:
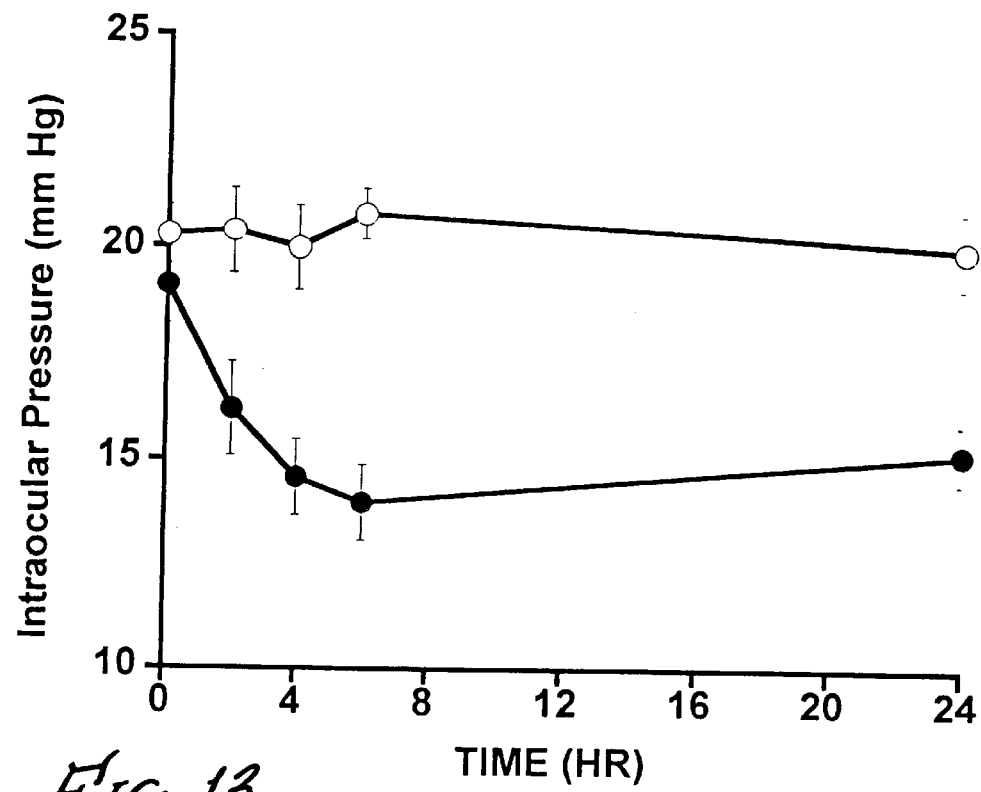
FIG. 13 is a graph showing the effect of 0.1% $PGF_{2\alpha}$ 1-ethanolamide (●) on dog intraocular pressure. Contralateral eyes received vehicle (○) as a control. Points are mean values±SEM; n=6.
Figure 14:
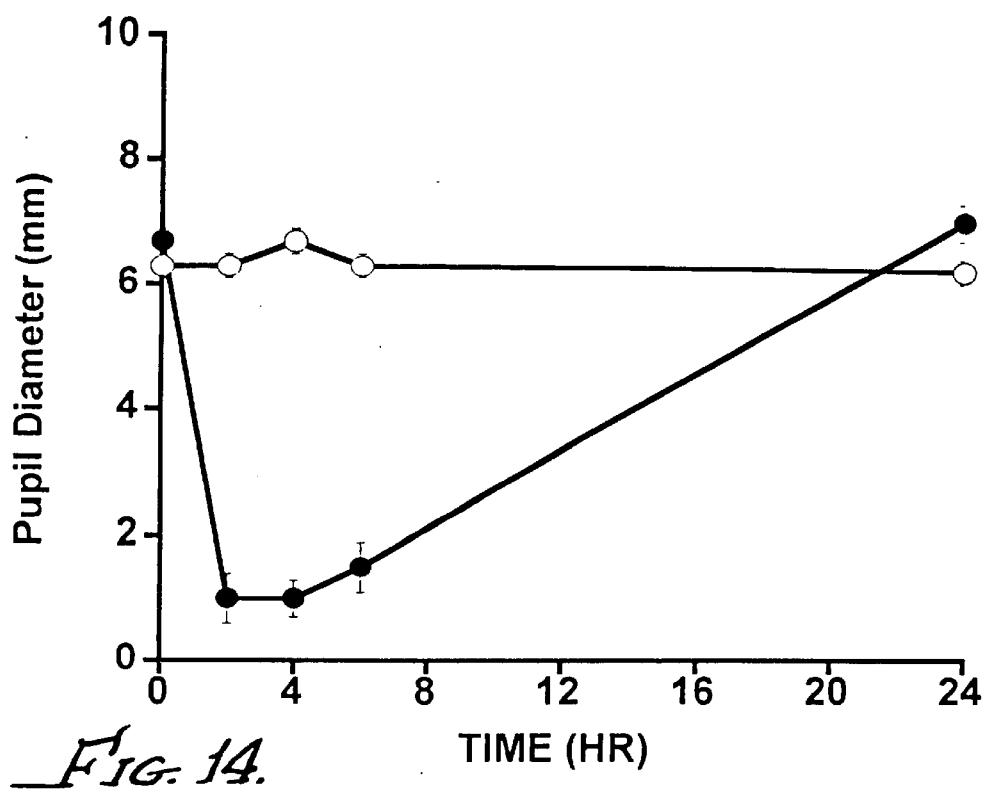
FIG. 14 is a graph showing the effect of 0.1% $PGF_{2\alpha}$ 1-ethanolamide (●) on dog pupil diameter. Contralateral eyes received vehicle (○) as a control. Points are mean values±SEM; n=6.
Figure 15:
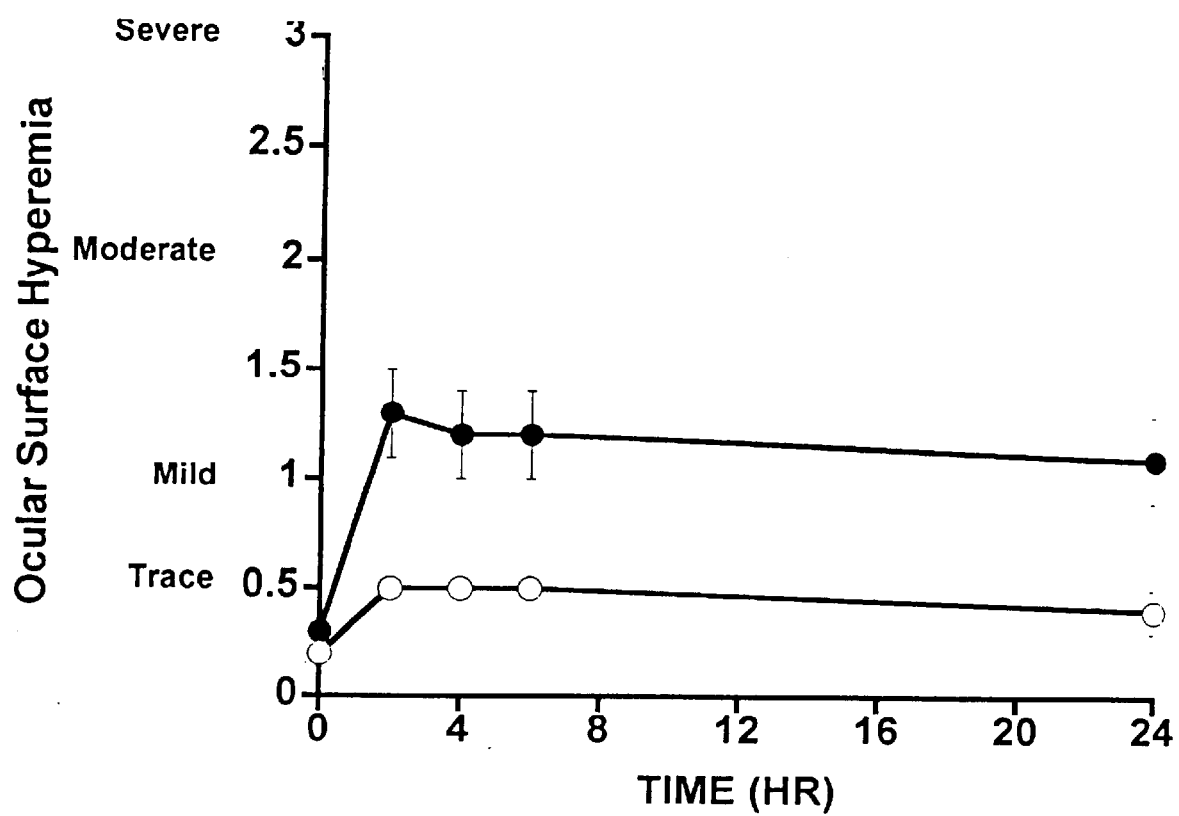
FIG. 15 is a graph showing the effect of $PGF_{2\alpha}$ 1-ethanolamide (●) on dog ocular surface hyperemia. Contralateral eyes received vehicle (○) as a control. Points are mean values±SEM; n=6.

The ocular effects of PGF$_{2\alpha}$ 1-ethanolamide were studied in dogs. PGF$_{2\alpha}$ 1-ethanolamide at a 0.1% dose produced a marked and highly significant decrease in intraocular pressure (FIG. 13; Table 14). The effect persisted over the entire 24 hr experimental period. PGF$_{2\alpha}$ 1-ethanolamide also caused marked miosis (FIG. 14; Table 15). Unlike the ocular hypotensive effect, the decrease in pupil diameter had resolved by the 24 hr time point. PGF$_{2\alpha}$ 1-ethanolamide caused mild ocular surface hyperemia, compared to trace for vehicle, throughout the 24 hr experimental period (FIG. 15; Table 16).

In the ensuing Tables, unless indicated otherwise, the concentration of the test or control compounds is indicated by the logarithmic exponent only. Thus and by way of example "–8" in the Tables means 10$^{-8}$ M concentration of the test or control substance.

TABLE 1

Effect of graded doses of PGF$_{2\alpha}$ 1-ethanolamide on the isolated feline iris sphincter smooth muscle. Reference contraction was provided by 10$^{-7}$ M PGF$_{2\alpha}$. Values are mean ± SEM; n = 4

| | Prostaglandin F$_{2\alpha}$ 1-ethanolamide concentration, log [M] | | | |
| --- | --- | --- | --- | --- |
| | –8 | –7 | –6 | –5 |
| % Maximal contractile response mean χ ± SEM | 2.7 ± 1.7 | 77 ± 5.5 | 119.2 ± 6.0 | 126.0 ± 3.6 |

TABLE 2

Inhibitory effect of graded doses of PGF$_{2\alpha}$ 1-ethanolamide on field stimulated contraction of the isolated guinea pig vas deferens. Values are mean ± SEM; n= 4

| | Prostaglandin F$_{2\alpha}$ 1-ethanolamide concentration, log [M] | | | |
| --- | --- | --- | --- | --- |
| | –8 | –7 | –6 | –5 |
| % Maximal inhibition of responses mean χ ± SEM | 2.2 ± 1.3 | 12.5 ± 6.2 | 37.7 ± 8.4 | 98.5 ± 1.0 |

TABLE 3

Effect of graded doses of PGF$_{2\alpha}$ 1-ethanolamide on the isolated chick ileum. Reference contraction was provided by 10$^{-6}$ M PGE$_2$. Values are mean ± SEM; n = 4

| | Prostaglandin F$_{2\alpha}$ 1-ethanolamide concentration, log [M] | | | |
| --- | --- | --- | --- | --- |
| | –8 | –7 | –6 | –5 |
| % Maximal contractile response mean χ ± SEM | 0 ± 0 | 15.0 ± 8.4 | 50.7 ± 4.0 | 66.5 ± 9.4 |

TABLE 4

Effect of graded doses of PGF$_{2\alpha}$ 1-ethanolamide on the isolated guinea pig ileum. Reference contraction was provided by PGE$_2$ 10$^{-6}$ M. Values are mean ± SEM; n = 4

| | Prostaglandin F$_{2\alpha}$ 1-ethanolamide concentration, log [M] | | | |
| --- | --- | --- | --- | --- |
| | –8 | –7 | –6 | –5 |
| % Maximal response mean χ ± SEM | 0 ± 0 | 0 ± 0 | 4.0 ± 2.6 | 9.7 ± 4.2 |

TABLE 5

Effect of graded doses of $PGF_{2\alpha}$ 1-ethanolamide on the isolated rat aorta. Reference contraction was provided by $10^{-7}$ M U-46619. Values are mean ± SEM; n = 4

| | Prostaglandin $F_{2\alpha}$ 1-ethanolamide concentration, log [M] | | | |
|---|---|---|---|---|
| | −8 | −7 | −6 | −5 |
| % Maximal contractile response mean $\chi$ ± SEM | 0 ± 0 | 0 ± 0 | 4.0 ± 2.6 | 9.7 ± 4.2 |

TABLE 6

Effect of graded doses of prostaglandin $F_{2\alpha}$ 1-ethanolamide on platelet aggregation and inhibition of ADP induced aggregation. Reference responses are provided by $2 \times 10^{-5}$ M ADP. Values are mean ± SEM; n = 4

| | Prostaglandin $F_{2\alpha}$ 1-ethanolamide concentration, log [M] | | |
|---|---|---|---|
| | −7 | −6 | −5 |
| % Platelet aggregation | 0 ± 0 | 0 ± 0 | 0 ± 0 |
| % Inhibition platelet aggregation | 0 ± 0 | 0 ± 0 | 0 ± 0 |

TABLE 7

Increases in intracellular free $Ca^{2+}$ concentration $[Ca^{2+}]_i$ produced by graded doses of prostaglandin $F_{2\alpha}$ 1-ethanolamide and prostaglandin $F_{2\alpha}$ in CRL 1497 human dermal fibroblasts. Values are mean ± SEM; n = 4

| | −9 | −8 | −7 | −6 | −5 |
|---|---|---|---|---|---|
| | Prostaglandin $F_{2\alpha}$ 1-ethanolamide concentration, log [M] | | | | |
| $\Delta[Ca^{2+}]_i$ mean $\chi$ ± SEM | — | 3.4 ± 1.5 | 13.5 ± 3.9 | 45.8 ± 11.5 | 97.9 ± 10.8 |
| | Prostaglandin $F_{2\alpha}$ concentration, log [M] | | | | |
| $\Delta[Ca^{2+}]_i$ mean $\chi$ ± SEM | 5.6 ± 2.4 | 47.7 ± 9.4 | 124.1 ± 6.5 | 127.4 ± 7.6 | 136.7 ± 11.2 |

TABLE 8

Vasorelaxation of the pre-contracted rabbit jugular vein segment by prostaglandin $F_{2\alpha}$ 1-ethanolamide and prostaglandin $F_{2\alpha}$. Reference vasorelaxation is provided by $PGE_2$ $10^{-7}$ M. Values are mean ± SEM; n = 6 for $PGF_{2\alpha}$ 1-ethanolamide, n = 7 for $PGF_{2\alpha}$.

| | Prostaglandin $F_{2\alpha}$ 1-ethanolamide concentration, log [M] | | | | | |
|---|---|---|---|---|---|---|
| | −10 | −9 | −8 | −7 | −6 | −5 |
| % relaxation mean $\chi$ ± SEM | 100 ± 0 | 99.7 ± 0.3 | 93.2 ± 2.2 | 80.3 ± 3.2 | 54.3 ± 10.2 | 38.4 ± 11.3 |
| | Prostaglandin $F_{2\alpha}$ concentration, log [M] | | | | | |
| | −11 | −10 | −9 | −8 | −7 | −6 |
| % relaxation mean $\chi$ ± SEM | 98 ± 1.1 | 92.5 ± 2.3 | 71.9 ± 7.2 | 25.8 ± 7.8 | 8.3 ± 3.0 | 6.7 ± 2.7 |

TABLE 9

Increases in intracellular free $Ca^{2+}$ concentration $[Ca^{2+}]_i$ produce by graded doses of prostaglandin $F_{2\alpha}$ 1-ethanolamide and prostaglandin $F_{2\alpha}$ in HEK-293 cells stably transfected with the recombinant feline FP receptor. Values are mean ± SEM; n = 3.

|  | −10 | −9 | −8 | −7 | −6 | −5 |
|---|---|---|---|---|---|---|
| | Prostaglandin $F_{2\alpha}$ 1-ethanolamide concentration, log [M] | | | | | |
| $\Delta[Ca^{2+}]_i$ mean $\chi$ ± SEM | — | — | 0 ± 0 | 28.5 ± 3.1 | 45.2 ± 6.4 | 77.2 ± 14.7 |
| | Prostaglandin $F_{2\alpha}$ 1-ethanolamide concentration, log [M] | | | | | |
| $\Delta[Ca^{2+}]_i$ mean $\chi$ ± SEM | 6.5 ± 5.0 | 22.2 ± 6.4 | 45.7 ± 5.3 | 78.8 ± 8.3 | 87.9 ± 9.0 | 85.0 ± 9.6 |

TABLE 10

Total inositol phosphate accumulation produced by graded doses of prostaglandin $F_{2\alpha}$ 1-ethanolamide and 17-phenyl prostaglandin $F_{2\alpha}$ in HEK-293 cells stably transfected with the recombinant feline FP receptor. Reference stimulation was provided by 17-phenyl $PGF_{2\alpha}$ $10^{-6}$ M. Values are mean ± SEM; n = 3 for $PGF_{2\alpha}$ 1-ethanolamide and 4 for 17-phenyl $PGF_{2\alpha}$ of experiments performed in duplicate.

|  | −9 | −8 | −7 | −6 | −5 |
|---|---|---|---|---|---|
| | Prostaglandin $F_{2\alpha}$ 1-ethanolamide concentration, log [M] | | | | |
| % maximal total inositol phosphate formation mean $\chi$ ± SEM | — | 3.9 ± 3.2 | 14.9 ± 4.7 | 63.0 ± 16.4 | 89.2 ± 4.8 |
| | 17-phenyl Prostaglandin $F_{2\alpha}$ concentration, log [M] | | | | |
| % maximal total inositol phosphate formation mean $\chi$ ± SEM | 17.8 ± 6.4 | 56.8 ± 10.8 | 89.7 ± 2.4 | 99.9 ± 1.1 | — |

TABLE 11

Total inositol phosphate accumulation produced by graded doses of prostaglandin $F_{2\alpha}$ 1-ethanolamide and 17-phenyl prostaglandin $F_{2\alpha}$ in HEK-293 cells stably transfected with the recombinant human FP receptor. Reference stimulation was provided by 17-phenyl $PGF_{2\alpha}$ $10^{-6}$ M. Values are mean ± SEM; n = 3 for $PGF_{2\alpha}$ 1-ethanolamide and 4 for 17-phenyl $PGF_{2\alpha}$ of experiments performed in duplicate.

|  | −9 | −8 | −7 | −6 | −5 |
|---|---|---|---|---|---|
| | Prostaglandin $F_{2\alpha}$ 1-ethanolamide concentration, log [M] | | | | |
| % maximal total inositol phosphate accumulation mean $\chi$ ± SEM | — | 0.3 ± 0.6 | 10.0 ± 1.6 | 48.4 ± 3.3 | 85.0 ± 1.9 |
| | 17-phenyl Prostaglandin $F_{2\alpha}$ concentration, log [M] | | | | |
| % maximal total inositol phosphate accumulation mean $\chi$ ± SEM | 14.7 ± 3.3 | 57.8 ± 2.0 | 92.3 ± 0.9 | 100 ± 1.3 | — |

TABLE 12

Radioligand binding competition studies ($PGF_{2\alpha}$ 1-ethanolamide and 17-phenyl $PGF_{2\alpha}$ vs. 5nM $^3$H-17-phenyl $PGF_{2\alpha}$) on the recombinant feline FP receptor. Values are mean ± SEM; n = 3 of experiments performed in duplicate.

| | Prostaglandin $F_{2\alpha}$ 1-ethanolamide concentration, log [M] | | | | |
|---|---|---|---|---|---|
| | −9 | −8 | −7 | −6 | −5 |
| % specific binding mean $\chi$ ± SEM | 89.7 ± 3.2 | 93.7 ± 3.8 | 89.7 ± 4.9 | 48.0 ± 2.9 | 8.3 ± 4.8 |

| | 17-phenyl Prostaglandin $F_{2\alpha}$ concentration, log [M] | | | | | |
|---|---|---|---|---|---|---|
| | −10 | −9 | −8 | −7 | −6 | −5 |
| % specific binding mean $\chi$ ± SEM | 92.7 ± 6.9 | 80.7 ± 7.1 | 43.7 ± 1.5 | 17.0 ± 6.5 | 10.3 ± 8.9 | 0 ± 0 |

TABLE 13

Radioligand binding competition studies ($PGF_{2\alpha}$ 1-ethanolamide and 17-phenyl $PGF_{2\alpha}$ vs. 5nM $^3$H-17-phenyl $PGF_{2\alpha}$) on the recombinant human FP receptor. Values are mean ± SEM; n = 3 of experiments performed in duplicate.

| | Prostaglandin $F_{2\alpha}$ 1-ethanolamide concentration, log [M] | | | | |
|---|---|---|---|---|---|
| | −9 | −8 | −7 | −6 | −5 |
| % specific binding mean $\chi$ ± SEM | 94.7 ± 1.4 | 103.3 ± 0.3 | 95.9 ± 1.5 | 63.7 ± 2.7 | 19.7 ± 1.2 |

| | 17-phenyl Prostaglandin $F_{2\alpha}$ concentration, log [M] | | | | | |
|---|---|---|---|---|---|---|
| | −10 | −9 | −8 | −7 | −6 | −5 |
| % specific binding mean $\chi$ ± SEM | 98 ± 1.1 | 65.0 ± 1.0 | 24.0 ± 1.2 | 5.3 ± 1.5 | 1.7 ± 1.7 | 0 ± 0 |

TABLE 14

Effect of 0.1% Prostaglandin $F_{2\alpha}$ 1-ethanolamide on dog intraocular pressure. Values are mean ± SEM; n = 6. **$p < 0.01$ significant change from baseline intraocular pressure according to Student's paired t test.

| | | Times of intraocular pressure measurement (HR) | | | | |
|---|---|---|---|---|---|---|
| | | 0 | 2 | 4 | 6 | 24 |
| Intraocular pressure (mm Hg) mean $\chi$ ± SEM | Test eye | 19.1 ± 0.9 | 16.2 ± 1.1** | 14.6 ± 0.9** | 14.0 ± 0.9** | 15.2 ± 0.7** |
| | Vehicle control eye | 20.3 ± 0.7 | 20.4 ± 1.0 | 20.0 ± 1.0 | 20.8 ± 0.6 | 20.0 ± 0.9 |

TABLE 15

Effect of 0.1% Prostaglandin $F_{2\alpha}$ 1-ethanolamide on dog pupil diameter. Values are mean ± SEM; n = 6. **p < 0.01 significant change from baseline pupil diameter according to Student's paired t test.

| | | Times of pupil diameter measurement (HR) | | | | |
|---|---|---|---|---|---|---|
| | | 0 | 2 | 4 | 6 | 24 |
| Pupil diameter (mm) | Test eye | 6.7 ± 0.2 | 1.0 ± 0.4** | 1.0 ± 0.3** | 1.5 ± 0.4** | 7.0 ± 0.3 |
| | Vehicle control eye | 6.3 ± 0.2 | 6.3 ± 0.2 | 6.7 ± 0.2 | 6.3 ± 0.2 | 6.2 0.2 |

TABLE 16

Effect of 0.1% Prostaglandin $F_{2\alpha}$ 1-ethanolamide on dog ocular surface hyperemia. Values are mean ± SEM; n = 6.

| | | Times of ocular surface hyperemia measurement (HR) | | | | |
|---|---|---|---|---|---|---|
| | | 0 | 2 | 4 | 6 | 24 |
| Ocular Surface Hyperemia Score | Test eye | 0.3 ± 0.1 | 1.3 ± 0.2 | 1.2 ± 0.2 | 1.2 ± 0.2 | 1.1 ± 0.2 |
| | Vehicle control eye | 0.2 ± 0.1 | 0.5 ± 0 | 0.5 ± 0 | 0.5 ± 0 | 0.4 ± 0.1 |

Pharmaceutical Compositions, Methods of Use

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system, a substantially neutral pH being preferred. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable opthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| ingredient | amount (% w/v) |
|---|---|
| active ingredient | about 0.001–5 |
| preservative | 0–0.10 |
| vehicle | 0–40 |
| tonicity adjustor | 0–10 |
| buffer | 0.01–10 |
| pH adjustor | Q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution.

Especially preservative-free solutions are often formulated in non-resealable containers containing up to about ten, preferably up to about five units doses, where a typical unit dose is from one to about 8 drops, preferably one to about 3 drops. The volume of one drop usually is about 20–35 μl.

DETAILED DESCRIPTION OF SYNTHETIC PROCEDURES

$PGF_{2\alpha}$ (Free Carboxylic Acid)

To a stirred solution of 20 g $PGF_{2\alpha}$ tromethamine salt (51.9 mmol) in 150 ml $H_2O$ was added concentrated HCl such that the pH of the solution was adjusted to 2. The solution was extracted with 3×200 ml chloroform and concentrated in vacuo. $PGF_{2\alpha}$ free carboxylic acid appeared primarily as a solid layered between the aqueous and organic phases. The solid was collected from this layer and combined with solid obtained by filtration from the concentrated chloroform solution, and the combined solids were washed with 50% chloroform/methanol.

$PGF_{2\alpha}$ methyl ester; methyl (5Z,8α, 9α, 11α,13E, 15S)-9,11,15-trihydroxyprosta-5,13-dien-1-oate To a stirred solution of $PGF_{2\alpha}$ free carboxylic acid (2.528 g, 7.13 mmol) in 50 ml acetone was added 3.2 ml 1,8-diazabicyclo [5.4.0] undec-7-ene (21.39 mmol) and 1.33 ml iodomethane (21.39 mmol). The solution was stirred overnight, diluted with 150 ml ethyl aceate, washed with 2×50 ml 0.5 m LiOH, 1×50 ml brine and concentrated in vacuo to yield the title compound, pure methyl ester (purity checked by $^1H$ NMR).

$H^1$ NMR ($CDCl_3$): 5.56–5.34 (m, 4H), 4.01 (m, 1H), 3.87 (m, 1H), 3.87 (m, 1H), 3.63 (s, 3H), 3.18 (t, 2H, J=5.8 Hz), 2.31–2.02 (m, 8H), 1.69–1.25 (m, 12H), 0.849 (t, 3H, J=6.7 Hz).

$PGF_{2\alpha}$ 1-ethanolamide; (5Z,8α,9α,11α,13E,15S)-9,11,15-trihydroxy-N-(2-hydroxyethyL)prosta-5,13-dien-1-amide To a stirred solution of $PGF_{2\alpha}$ methyl ester (235.4 mg, 0.639 mmol) in 4.5 ml anhydrous methanol was added 771 μl ethanolamine (12.78 mmol). The tube containing the mixture was sealed and heated at 50° C. overnight. An aliquot was taken, concentrated in high vacuum with heat to remove excess ethanolamine and analyzed by $^1H$ NMR. The reaction was indicated to be 80% complete. The solution was concentrated under high vacuum at 65° C. for 1.5 hr, then at 60° C. overnight by Kugehlrohr distillation to remove residual ethanolamine. $^1H$ NMR and TLC in 5% methanol/ethylacetate indicated removal of the ethanolamine. (methyl ester $R_f$=0.41, $PGF_{2\alpha}$ 1-ethanolamide $R_f$=0.04). The crude material was flash chromatographed with 5% methanol/ethyl acetate to recover the remaining unreacted starting material, methyl ester in fractions 4–8 and 50%, and in methanol/ethyl acetate to yield the desired title compound in fractions 11–18. Further flash chromatography of fractions 11–18 with 15% methanol/ethyl acetate yielded the title compound free of starting material but still contaminated with with the C15 epimer in some fractions (fractions 7–10), and the desired product in pure state (in fractions 11–20). The $^1H+^{13}C$ NMR spectra of the title compound and its C 15 epimer are identical. Theoretical yield=254.0 mg, actual yield obtained=205.6 mg, 81%.

$H^1$ NMR ($CD_3OD$): 5.4–5.2 (m, 4H), 3.98 (m, 1H), 3.89 (m, 1H), 3.72 (m, 1H), 3.47 (t, 2H, J=5.8 Hz,), 3.18 (t, 2H, J=5.8 Hz), 2.24–1.90 (m, 8H), 1.50–1.21 (m, 12H), 0.796 (t, 3H, J=6.5 Hz).

What is claimed is:

1. A compound of the formula

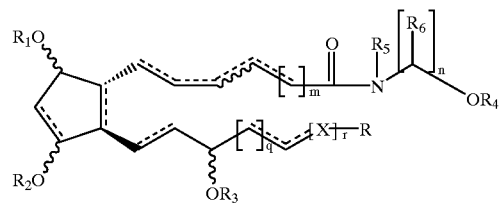

wherein the dashed lines represent absence of a bond, or a bond with the proviso that there are no two adjacent double bonds in the formula;

the wavy line attachments represent either alpha (α, down) or beta (β, up) configuration, where the wavy lines are attached to a double bond they represent either Z(cis) or E(trans) configuration;

the hatched lines indicate alpha (α) configuration and solid triangles indicate beta (β) configuration;

m is an integer having the values of 0 to 5;

n is an integer having the values 1–6, with the proviso that the compound represented by the formula is not $PGF_{2\alpha}$ 1-ethanolamide;

q and r each independently are integers having the value of 0 to 6;

X is $CH_2$, O or S with the proviso that when X is O or S then the dashed line adjacent to X represents absence of a bond;

R is $CH_3$, phenyl, furyl, thienyl, cycloalkl of 3 to 8 carbons, or phenyl furyl or thienyl itself substituted with one or two substituents selected from the group consisting of F, Cl, Br, alkyl of 1 to 6 carbons, $NO_2$, CN, COOH and COOalkyl where alkyl has 1 to 6 carbons;

$R_1$, $R_2$, $R_3$, and $R_4$ each independently represent H, a straight or branch-chained alkanoyl group having 1 to 6 carbons, benzoyl or lower alkyl of 1 to 6 carbons;

$R_5$ is H or straight or branch-chained alkyl group having 1 to 6 carbons, and $R_6$ is H or straight or branch-chained alkyl of 1 to 4 carbons or a pharmaceutically acceptable salt of said compound, and said compounds being active to lower intraocular pressure in the eye of a mammal but do not exert their ocular hypotensive activity through the FP prostaglandin receptor.

2. A Compound in accordance with claim 1 having the formula

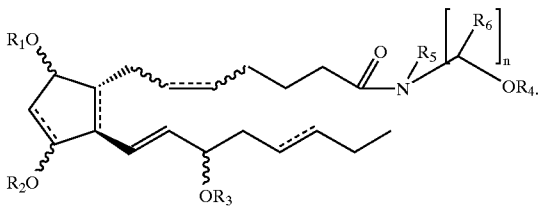

3. A compound in accordance with claim 2 where the dashed lines between carbons 10 and 11, 8 and 12 and 17 and 18 represent absence of a bond, and between carbons 5 and 6 represent a bond.

4. A compound in accordance with claim 2 where $R_5$ is H or lower alkyl of 1 to 3 carbons.

5. A compound in accordance with claim 4 where $R_5$ is H.

6. A compound in accordance with claim 2 where $R_6$ is H or lower alkyl of 1 to 3 carbons.

7. A compound in accordance with claim 6 where $R_6$ is H.

8. A compound in accordance with claim 2 where n is 2.

9. A compound in accordance with claim 2 where the configuration of the $OR_1$, $OR_2$ and $OR_3$ groups is alpha, the dashed line between the 5 and 6 positions represents a bond and the configuration of the 5–6 double bond is Z(cis).

10. A compound of the formula

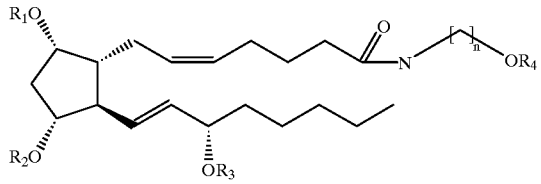

where $R_1$, $R_2$, $R_3$, and $R_4$ each independently represent H, a straight or branch-chained alkanoyl group having 1 to 6 carbons, benzoyl or straight or branch-chained alkyl having 1 to 6 carbons;

n is an integer having the values 1 to 6;

said compounds being active to lower intraocular pressure in the eye of a mammal but do not exert their ocular hypotensive activity through the FP prostaglandin receptor, with the proviso that that when n is 2, then at least one of the $R_1$, $R_2$, $R_3$, and $R_4$ groups is not H.

11. An isolated, substantially pure chemical substance having the formula

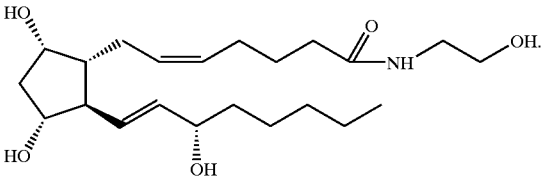

12. A pharmaceutical composition effective for lowering intraocular pressure in the eye of a mammal in need of treatment by such composition, the composition comprising as its active ingredient an effective amount of one or more compounds of the formula,

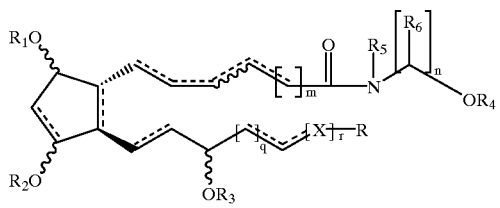

wherein the dashed lines represent absence of a bond, or a bond with the proviso that there are no two adjacent double bonds in the formula;

the wavy line attachments represent either alpha (α, down) or beta (β, up) configuration, where the wavy lines are attached to a double bond they represent either Z(cis) or E(trans) configuration;

the hatched lines indicate alpha (α) configuration and solid triangles indicate beta (β) configuration;

m is an integer having the values of 0 to 5;

n is an integer having the values 1–6;

q and r each independently are integers having the value of 0 to 6;

X is $CH_2$, O or S with the proviso that when X is O or S then the dashed line adjacent to X represents absence of a bond;

R is $CH_3$, phenyl, furyl, thienyl, cycloalkyl of 3 to 8 carbons, or phenyl furyl or thienyl itself substituted with one or two substituents selected from the group consisting of F, Cl, Br, alkyl of 1 to 6 carbons, $NO_2$, CN, COOH and COOalkyl where alkyl has 1 to 6 carbons;

$R_1$, $R_2$, $R_3$, and $R_4$ each independently represent H, a straight or branch-chained alkanoyl group having 1 to 6 carbons, benzoyl or lower alkyl of 1 to 6 carbons;

$R_5$ is H or straight or branch-chained alkyl group having 1 to 6 carbons; $R_6$ is H or straight or branch-chained alkyl of 1 to 4 carbons or a pharmaceutically acceptable salt of said compound, and said compounds being active to lower intraocular pressure in the eye of a mammal but do not exert their ocular hypotensive activity through the FP prostaglandin receptor, and a pharmaceutically acceptable excipient.

13. A pharmaceutical composition in accordance with claim 12 wherein the active compound has the formula

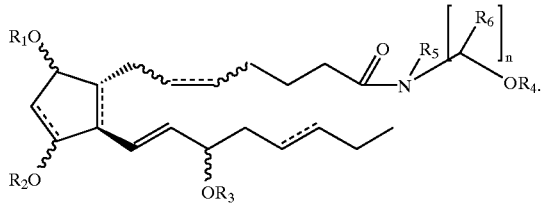

14. A pharmaceutical composition in accordance with claim 13 wherein in the formula of the active compound the dashed lines between carbons 10 and 11, 8 and 12 and 17 and 18 represent absence of a bond, and between carbons 5 and 6 represent a bond.

15. A pharmaceutical composition in accordance with claim 13 wherein in the formula of the active compound $R_5$ is H or lower alkyl of 1 to 3 carbons.

16. A pharmaceutical composition in accordance with claim 15 wherein in the formula of the active compound where $R_5$ is H.

17. A pharmaceutical composition in accordance with claim 13 wherein in the formula of the active compound $R_6$ is H or lower alkyl of 1 to 3 carbons.

18. A pharmaceutical composition in accordance with claim 17 wherein in the formula of the active compound where $R_6$ is H.

19. A pharmaceutical composition in accordance with claim 13 wherein in the formula of the active compound n is 2.

20. A pharmaceutical composition in accordance with claim 13 wherein in the formula of the active compound the configuration of the $OR_1$, $OR_2$ and $OR_3$ groups is alpha, the dashed line between the 5 and 6 positions represents a bond and the configuration of the 5–6 double bond is Z(cis).

21. A pharmaceutical composition in accordance with claim 13 wherein the active compound has the formula

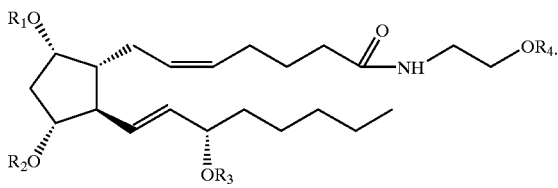

22. A pharmaceutical composition in accordance with claim 21 wherein the active compound has the formula

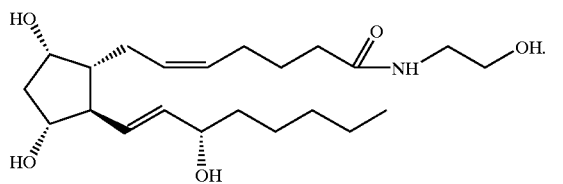

23. A pharmaceutical composition in accordance with claim 12 adapted for topical administration to the mammalian eye.

24. A pharmaceutical composition in accordance with claim 13 adapted for topical administration to the mammalian eye.

25. A pharmaceutical composition in accordance with claim 21 adapted for topical administration to the mammalian eye.

26. A pharmaceutical composition in accordance with claim 22 adapted for topical administration to the mammalian eye.

27. A method of lowering intraocular pressure in the eye of a mammal in need of such treatment, the method comprising the step of administering to the mammal a pharmaceutical composition comprising a pharmaceutically acceptable excipient and as its active ingredient an effective amount of one or more compounds of the formula,

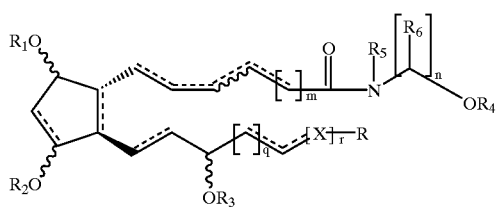

wherein the dashed lines represent absence of a bond, or a bond with the proviso that there are no two adjacent double bonds in the formula;

the wavy line attachments represent either alpha (α, down) or beta (β, up) configuration, where the wavy lines are attached to a double bond they represent either Z(cis) or E(trans) configuration;

the hatched lines indicate alpha (α) configuration and solid triangles indicate beta (β) configuration;

m is an integer having the values of 0 to 5;

n is an integer having the values 1–6;

q and r each independently are integers having the value of 0 to 6;

X is $CH_2$, O or S with the proviso that when X is O or S then the dashed line adjacent to X represents absence of a bond;

R is $CH_3$, phenyl, furyl, thienyl, cycloalkyl of 3 to 8 carbons, or phenyl furyl or thienyl itself substituted with one or two substituents selected from the group consisting of F, Cl, Br, alkyl of 1 to 6 carbons, $NO_2$, CN, COOH and COOalkyl where alkyl has 1 to 6 carbons;

$R_1$, $R_2$, $R_3$, and $R_4$ each independently represent H, a straight or branch-chained alkanoyl group having 1 to 6 carbons, benzoyl or lower alkyl of 1 to 6 carbons;

$R_5$ is H or straight or branch-chained alkyl group having 1 to 6 carbons; $R_6$ is H or straight or branch-chained alkyl of 1 to 4 carbons or a pharmaceutically acceptable salt of said compound, and said compounds being active to lower intraocular pressure in the eye of a mammal but do not exert their ocular hypotensive activity through the FP prostaglandin receptor.

28. A method of treatment in accordance with claim 27 where the active compound has the formula

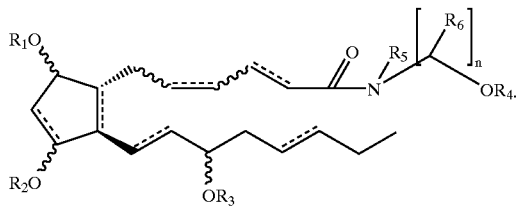

29. A method of treatment in accordance with claim 28 where the active compound has the formula

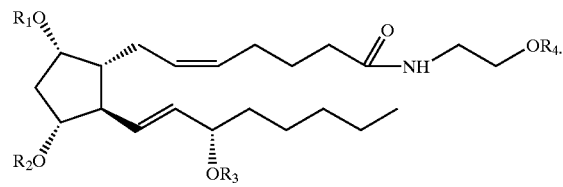

30. A method of treatment in accordance with claim 29 where the active compound has the formula

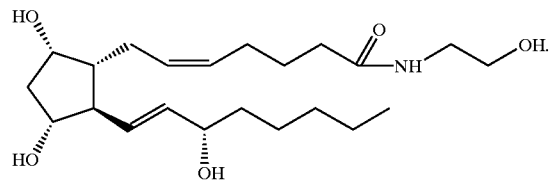

31. A method of treatment in accordance with claim 27 wherein the pharmaceutical composition is adapted for topical administration to the eye, and the method comprises administering said composition topically to the mammalian eye.

32. A method of treatment in accordance with claim 28 wherein the pharmaceutical composition is adapted for topical administration to the eye, and the method comprises administering said composition topically to the mammalian eye.

33. A method of treatment in accordance with claim 29 wherein the pharmaceutical composition is adapted for topical administration to the eye, and the method comprises administering said composition topically to the mammalian eye.

34. A method of treatment in accordance with claim 30 wherein the pharmaceutical composition is adapted for topical administration to the eye, and the method comprises administering said composition topically to the mammalian eye.

\* \* \* \* \*

UNITED STATES PATENT AND TRADEMARK OFFICE
CERTIFICATE OF CORRECTION

PATENT NO. : 6,395,787 B1  
DATED : May 28, 2002  
INVENTOR(S) : Woodward et al.

Page 1 of 2

It is certified that error appears in the above-identified patent and that said Letters Patent is hereby corrected as shown below:

Column 5,
Line 41, Formula 2,

" 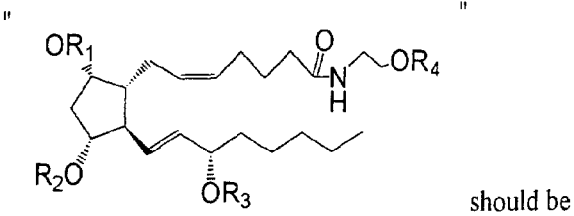 "    should be

-- 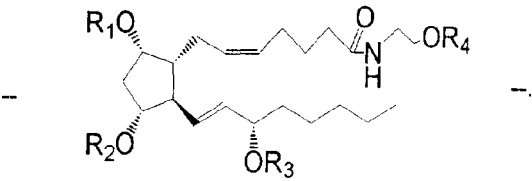 --.

Column 7,
Line 50, "C." should be -- C --.

Column 9,
Line 53, "C." should be -- C --.

Column 10,
Line 53, "C." should be -- C --.

Column 11,
Line 26, "C." should be -- C --.
Line 50, "C." should be -- C --.
Line 58, "C." should be -- C --.

Column 14,
Line 63, Table 4, "4.0 ± 2.6" should be -- 1.7 ± 1.0 --.
Line 63, Table 4, "9.7 ± 4.2" should be -- 15.8 ± 1.6 --.

UNITED STATES PATENT AND TRADEMARK OFFICE
CERTIFICATE OF CORRECTION

PATENT NO.     : 6,395,787 B1
DATED          : May 28, 2002
INVENTOR(S)    : Woodward et al.

It is certified that error appears in the above-identified patent and that said Letters Patent is hereby corrected as shown below:

Column 23,
Line 49, "C." should be -- C --.
Lines 53-54, both occurrences of "C." should be -- C --.

Column 28,
Line 36,

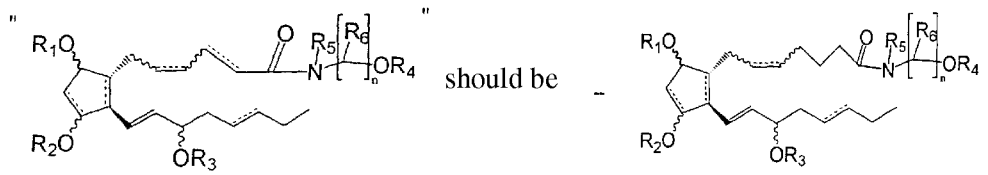

Signed and Sealed this

Twenty-ninth Day of October, 2002

*Attest:*

*Attesting Officer*

JAMES E. ROGAN
*Director of the United States Patent and Trademark Office*